(12) United States Patent
Gustafson et al.

(10) Patent No.: US 7,176,344 B2
(45) Date of Patent: Feb. 13, 2007

(54) SENSORING ABSORBING ARTICLE

(75) Inventors: Ingrid Gustafson, Åsa (SE); Carolyn Berland, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 616 days.

(21) Appl. No.: 10/655,344

(22) Filed: Sep. 5, 2003

(65) Prior Publication Data
US 2004/0113801 A1 Jun. 17, 2004

Related U.S. Application Data

(60) Provisional application No. 60/408,333, filed on Jun. 9, 2002.

(51) Int. Cl.
*A61F 13/15* (2006.01)
*G08B 23/00* (2006.01)
*G08B 21/00* (2006.01)

(52) U.S. Cl. .................. 604/361; 604/367; 340/573.5; 340/604

(58) Field of Classification Search ................ 604/361, 604/367, 362; 340/573, 571–604
See application file for complete search history.

(56) References Cited

U.S. PATENT DOCUMENTS

| | | | |
|---|---|---|---|
| 4,646,066 A | 2/1987 | Baughman et al. | |
| 5,348,761 A | 9/1994 | Mitter et al. | |
| 5,570,082 A | 10/1996 | Mahgerefteh et al. | |
| 5,821,129 A | 10/1998 | Grimes et al. | |
| 6,393,921 B1 | 5/2002 | Grimes et al. | |
| 6,397,661 B1 | 6/2002 | Grimes et al. | |
| 2002/0166382 A1 | 11/2002 | Bachas et al. | |
| 2004/0014201 A1* | 1/2004 | Kim et al. | ............... 435/287.2 |

FOREIGN PATENT DOCUMENTS

| | | |
|---|---|---|
| WO | WO 98/27417 | 6/1998 |
| WO | 00/00233 A1 | 1/2000 |
| WO | WO 00/00233 | 1/2000 |
| WO | WO 00/79497 | 12/2000 |
| WO | 02/078513 A2 | 10/2002 |
| WO | 03/027636 A2 | 4/2003 |
| WO | 2004/021944 | 3/2004 |
| WO | 2004/038342 | 5/2004 |

OTHER PUBLICATIONS

PCT International Search Report dated Nov. 12, 2003.
C. A. Grimes et al.—Thin-Film Magnetoelastic Microsensors for Remote Query Biomedical Monitoring, Biomedical Microdevices, 1999, No. 2:1, pp. 51-60.

(Continued)

*Primary Examiner*—Jacqueline Stephens
(74) *Attorney, Agent, or Firm*—Buchanan Ingersoll & Rooney PC

(57) ABSTRACT

A disposable sensoring absorbent structure for detecting wetness comprises at least one absorbent layer and at least one sensing device comprising a magnetoelastic film. Such an absorbent structure enables the monitoring the status, e.g., wetness and/or at least one biological and/or chemical analyte, in an absorbent article. A change in status, such as wetness, may reflect an event, such as urination or a feces event. Also included are methods for detecting wetness and/or at least one biological and/or at least one chemical analyte, using the sensoring absorbent structure according to an embodiment of the invention.

35 Claims, 30 Drawing Sheets

OTHER PUBLICATIONS

C. A. Grimes et al.—Remote Query Measurement of Pressure, Fluid-Flow Velocity, and Humidity Using Magnetoelastic Thick-Film Sensors, Sensors and Actuators, 2000, No. 84, pp. 205-212.

Q. Y. Cai et al., "A Remote Query Magnetoelastic pH Sensor", Sensors and Actuators, B71:112-117 (2000), Elsevier Science B.V.

C.A. Grimes et al., "Remote Query Measurement of Pressure, Fluid-Flow Velocity, and Humidity Using Magnetoelastic Thick-Film Sensors", Sensors and Actuators, 84:205-212 (2000), Elsevier Science S.A.

C.A. Grimes et al., "Thin-Film Magnetoelastic Microsensors for Remote Query Biomedical Monitoring", Biomedical Microdevices 2:1,51-60, (1999).

* cited by examiner

Excitation coil         Pick-up coil

Magnetoelastic film

SENSING ABSORBING ARTICLE

CROSS-REFERENCE TO RELATED APPLICATION

This application claims priority to U.S. Provisional Application No. 60/408,333, entitled "Sensing Absorbing Article," filed Sep. 6, 2002, the entire content of which is hereby incorporated by reference.

TECHNICAL FIELD

The present invention relates to a sensing absorbent structure, comprising at least one absorbent layer and at least one sensing device comprising a magnetoelastic film. Also provided is a sensing absorbent system and a method for detecting wetness and/or at least one biological and/or chemical analyte in an absorbent structure.

BACKGROUND OF THE INVENTION

Disposable Absorbent Articles

Absorbent articles, such as diapers for infants and adults, sanitary napkins, and adult incontinence briefs, are well known within the art and used widely. Most such products today are used on a single-use basis. The single-use basis of such disposable products have led to the development of a wide assortment of different products to meet specific requirements, e.g., in infant and toddler care, as well as in adults suffering from incontinence. The main purpose of such absorbent articles is normally to absorb, retain and isolate body wastes, i.e., urine, feces, or blood.

Detection of an Event

One specific group of absorbent articles may respond to an event, such as urination or defecation, after absorption onto or into the product. The response can be a signal after the event has occurred and is based on a measure of, e.g., wetness, or temperature. The signal of an event can give the user or nursing aid feedback that an event has occurred, to ease the handling for the user or care taker/nursing personnel.

U.S. Pat. No. 5,348,761 describes a moisture/wetness-detecting sensor that utilizes a swellable plastic having conductive additives. The sensor swells in operation in response to moisture, which, in turn, increases resistance in the sensor. All embodiments show connecting wires attached to electrodes for monitoring the moisture/wetness.

Chemical Detection

One group of absorbent articles known in the art comprises chemical reactive means, i.e., sensors, to detect various chemical substances such as pH or ions, in body waste(s), e.g., feces or urine. The detection of such chemical substances will give the user or nursing aid feedback that an event has occurred. Most chemical sensors rely on a color change to enable detection of, e.g., pH or different ions. Monitoring such color changes often also requires that the user, e.g., an elderly incontinent patient or an infant, be physically displaced, e.g., by turning to one side.

Furthermore, chemical compounds responsible for color changes are often toxic or irritating to the skin. Therefore, the incorporation of such compounds in absorbent articles is hardly appropriate, with respect to both environmental aspects as well as the user's health.

Biodetection

Another group of absorbent articles includes means for detecting biomolecules, such as proteins, hormones, microorganisms (e.g., bacteria or viruses), glucose or chemical substances excreted by the body as marker molecules due to metabolic conditions, e.g., glucose due to carbohydrate metabolism, and bacterial toxins. Several of these articles also detect and target potentially pathogenic microorganisms, such as bacteria, viruses, fungi, and parasites, e.g., protozoans. Detection of such biomolecules, e.g., microorganisms, can give indications of potential health and/or nutritional status, as well as detecting an event such as urination or defecation.

In WO 00/00233, a disposable article to be fitted to a wearer is disclosed comprising a biosensor with a biorecognition element to detect a biological analyte in body waste.

WO 98/27417 describes a biosensing device for detecting and quantifying analytes present in a medium. The analyte is detected via an image produced as a diffraction pattern.

Magnetoelastic Sensors

Magnetoelastic sensors have been described by Grimes et al., (Biomedical Microdevices, 2:51–60, 1999).

When a magnetic field is applied to, for instance, a ferromagnetic material, the dimension of the material changes. This effect is called magnetostriction. The size of the dimensional change of the material is governed by the magnetostriction constant.

When exposed to an externally applied magnetic pulse, the material generates magnetic flux with a characteristic resonant frequency. The magnetic flux can be detected remotely by a pick-up coil. The changes in resonant frequency can be monitored so as to measure or detect multiple environmental parameters. Measurements of temperature, pressure, viscosity, using this method are described in Grimes et al., (Biomedical Microdevices, 2:51–60, 1999). Through the inclusion of a glucose-responding mass changing polymer, in situ measurement of glucose levels can be performed.

It is also possible to excite the material with a continuous magnetic field showing a frequency corresponding to the magneto-acoustic resonant frequency and measure the response from the material. At this resonant frequency the response from the material is maximal. It also possible to excite the material with a continuous magnetic field with a frequency close to the magneto-acoustic resonance frequency in pulses and to measure the damped magnetic response from the material between the pulses.

Magnetoacoustic Effect

When a magnetic material is excited by a magnetic field, it stores magnetic energy in a magnetoelastic mode. When the field is switched off, the material shows damped oscillation with a specific frequency, the latter being the magnetoacoustic resonant frequency.

General Issues Concerning Sensors in Absorbent Articles

Sensors to be included in absorbent articles should preferably be inexpensive, to enable disposable single-use of the absorbent articles. Also, they should be reliable and able to withstand the particular milieu found in a very specific environment, such as a diaper.

Also, the sensor should be safe for the user and the nursing aid, i.e., not evoke any skin irritation or toxic effects in either party. Furthermore, it is recommended that the sensor be environmentally friendly, to make such an absorbent product disposable without any restrictions in waste handling. Environmental related concerns are becoming increasingly important to our society today, and are respectively lobbied for and implemented by international environmental regulatory agencies and national governments.

Several of the above-mentioned sensors require direct physical connections to the sensor, and/or the incorporation of an electronic circuit. This is inconvenient for the user in many aspects, not allowing for remote detection and monitoring, which will limit the usefulness of the sensor in several aspects. The electronic circuit requires that a power supply be incorporated into the absorbent article, which raises a health question for the user or nursing aid. Moreover, it is bulky to incorporate into the absorbent article. Also, the incorporation of one or more batteries into a disposable product is an environmental hazard, since battery disposal requires special recycling protocols.

The monitoring of an event should be done simply, to enable the user or nursing aid to easily register the body waste status, without having to physically displace the user in any way.

U.S. Pat. No. 5,821,129 discloses a sensor that allows for a remote, continuous magnetochemical detection of various chemical species in, e.g., exhaust pipes, flumes, chemical baths or body implants.

WO 00/79497 describes the use of a radiofrequency resonant circuit sensing device and its use for detection of fluid leaks from containers or bodies, e.g., fluid drainage from a human suffering from urinary and/or fecal incontinence. The sensor device relies on a coil which can receive the fluid and which responds by shortcircuiting in a "one hit" event after, e.g., urination.

It is thus highly desirable in light of the aforementioned problems to develop means and methods for monitering the status in an absorbent article, which, thus, reflect the status of the user in an easily detected, inexpensive, disposable way, and which also avoids earlier problems associated with the prior art means and methods. The present invention addresses these needs and interests.

SUMMARY

In view of the foregoing disadvantages known in the art when monitoring status in an absorbent article, embodiments of the present invention provide a sensing absorbent structure able to provide information about the status of the absorbent article in an easily monitored, inexpensive, disposable way. In some cases the status of the absorbent article thus reflects the status of the user.

One object of embodiments of the present invention is to provide a sensing absorbent article for detecting wetness.

Another object of the present invention is to provide a sensing absorbent article for detecting at least one biological and/or chemical analyte.

Thus, embodiments of the present invention provide an absorbent structure, comprising at least one absorbent layer and at least one sensing device comprising a magnetoelastic film.

The absorbent structure according to an embodiment of the invention is a structure wherein the at least one layer comprises 0–95% of superabsorbent material.

The magnetoelastic film in the absorbent structure according to an embodiment of the invention, oscillates with a magnetoacoustic resonant frequency, after the magnetoelastic film is excited in a magnetic field and when the magnetic field is switched off.

Furthermore, the at least one sensing device in the absorbent structure according to an embodiment of the invention may be 1–20 sensing device(s).

The magnetoelastic film in the absorbent structure according to an embodiment of the invention is a thin film, and the film is selected from the group consisting of magnetostrictive material, such as magnetoelastic material, soft magnetoelastic material, amorphous magnetoelastic material, and mixtures thereof.

Also, embodiments of the present invention provide an absorbent article such as a diaper, a pants-type diaper, incontinence garment, sanitary napkin, wipe, towel, tissue, bed protector, wound or sore dressing, or similar product comprising the absorbent structure according to the invention, a fluid-permeable top sheet, and an essentially fluid-impermeable bottom sheet.

In another aspect, an embodiment of the present invention provides a sensing absorbent system, comprising the absorbent structure according to an embodiment of the invention, optionally being part of the absorbent articles according to an embodiment of the invention, and a hand held unit, comprising an excitation coil generating a magnetic field to magnetize said magnetoelastic film and, optionally, a pick-up coil to detect the magnetoacoustic resonant frequency.

In a further aspect, a method for detecting wetness/moisture/humidity and/or at least one biological and/or chemical analyte is provided. Such a method comprises the steps of a) providing an absorbent structure according to an embodiment of the invention, an absorbent article according to an embodiment of the invention, or the system according to an embodiment of the invention, b) applying a magnetic field, c) exciting the magnetoelastic film in the at least one sensing device in the absorbent structure, d) switching the magnetic field off, e) recording magnetoacoustic resonant frequency, f) optionally repeating step b) to e), and g) detecting changes in the magnetoacoustic resonant frequency, so as to detect wetness/moisture/humidity and/or at least one biological and/or chemical analyte in the absorbent structure.

BRIEF DESCRIPTION OF THE FIGURES

FIG. 6A is a diaper with one sensing device 20 in the absorbent structure. FIG. 6B is a diaper with five sensing devices 20 placed in different parts of the absorbent structure. FIG. 6C is a diaper with four sensing devices 20 in the front of the diaper still in the absorbent structure.

DETAILED DESCRIPTION

Definitions

Figure 1A:
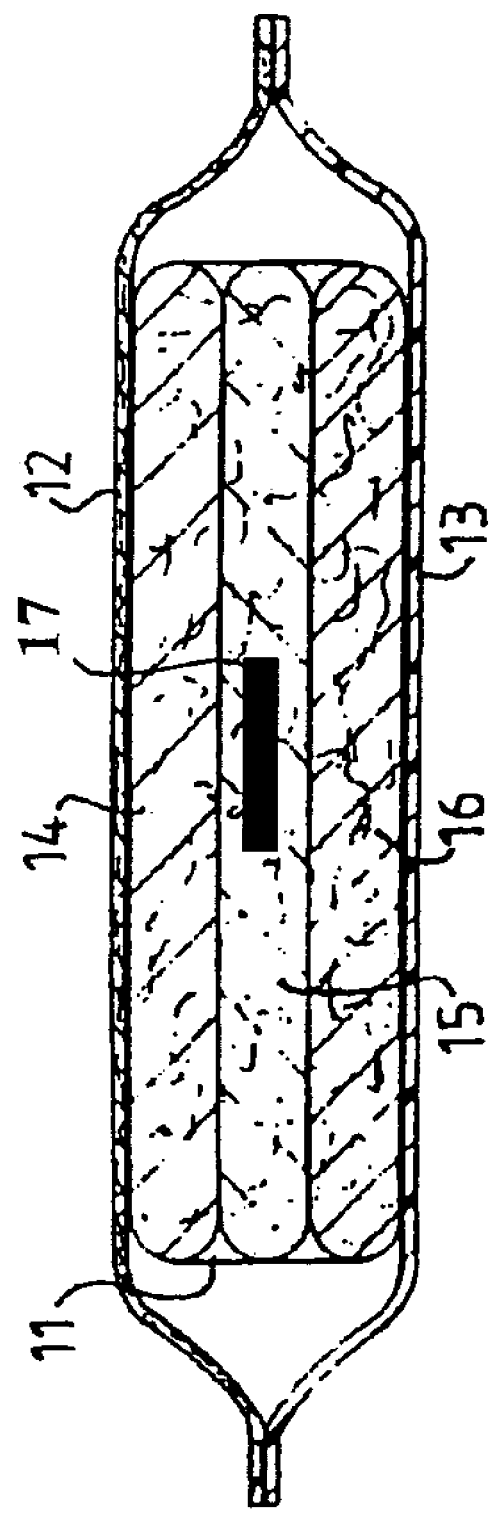
FIGS. 1A and 1B show embodiments of an absorbent structure 11 according to the invention, suitable for an absorbent article, such as a diaper. The absorbent structure 11 is enclosed in a conventional manner between a fluid-permeable layer 12 which may comprise a soft non-woven material, a perforated plastic film or the like and is intended to lie proximal to the wearer when used, and a fluid-impermeable bottom sheet 13. The sheets 12 and 13 have parts, which may extend beyond the absorbent body 11. The absorbent structure shown in FIGS. 1A and 1B has at least one sensing device comprising a magnetoelastic film 17 placed on different positions FIGS. 1A and B.

As used herein, the term "absorbent article" refers to a device that absorbs, retains, and contains body waste or body exudates. The device is placed against or in the proximity of the body of a wearer to absorb, retain and contain the various body waste or body exudates from the body.

The term "disposable" is herein intended to mean an absorbent article which is not intended to be laundered, restored, or reused as an absorbent article. Such an absorbent article is intended to be discarded after a single use. The single use does not exclude the product from being recycled, made compost, or otherwise disposed of in an environmentally compatible manner.

The term "sensor" is herein intended to mean a device that is capable of detecting an event or a parameter that is associated with an event. A parameter associated with an event is any measurable signal that correlates with the occurrence of an event within the framework of the system, i.e., a signal caused by the waste, the wearer, or a component thereof. Sensors include anything that responds to one or more specific inputs.

The term "sensoring" or "sensing" is herein intended to mean means and methods capable of detecting an event or a parameter that is associated with an event, e.g., via a sensoring device.

The term "wetness" is herein intended to mean the condition of being wet, humid, damp, or moist or the condition of containing or being covered by a liquid, especially water.

The term "diaper" is herein intended to mean an absorbent article generally worn about the lower part of the torso by infants, toddlers and incontinent persons.

The term "user" is herein intended to mean a) the user of an absorbent article or b) the nursing aid of the user of an absorbent article.

The term "magnetostriction" refers to a common phenomena for magnetic materials. Magnetostriction means that when a magnetic material is magnetized, the dimensions of the material change. The size of the dimensional change depends on temperature, magnetization in the material, and, of course, on the material properties. Magnetostriction is due to the interaction between the atomic magnetic moments in the material.

The term "magnetoacoustic resonant frequency" refers to an oscillation frequency. Such a frequency occurs when a magnetic material is excited by a magnetic field and stores magnetic energy in a magnetoelastic mode. When the magnetic field is switched off, the material shows damped oscillation with a specific frequency, refered to as the magnetoacoustic resonant frequency.

The term "biological analyte," "biomolecule," or "bioanalyte" is herein intended to mean biologically derived material. Examples of biological analytes, biomolecules, or bio-analytes include, but are not limited to, proteins, peptides, hormones, microorganisms (e.g., pathogenic and non-pathogenic bacteria, viruses, fungi, and parasites such as protazoans), parts of a cell membrane or capsid, lipids, carbohydrates including glucose and ketones, bacterial toxins, lectins, nutritional markers, nucleic acids including DNA and RNA, mammalian cells (e.g., blood cells such as lymphocytes and red blood cells), bilirubin, urobilinogen. Further examples are discussed below. Other biological analytes would be apparent to one skilled in the art.

The Absorbent Structure

In normal use, an absorbent structure in an absorbent article, such as a diaper, a pants-type diaper, incontinence garment, sanitary napkin, bed protector, wound or sore dressing, serves to absorb, retain and isolate body wastes or body exudates, for example, urine, feces, blood, menstruation blood, fluid matter from wounds and sores, rinsing fluid, and saliva.

As discussed above, the present invention relates to a sensing absorbent structure, wherein the sensor part will enable means and methods for monitoring status, e.g., by measuring wetness or humidity, in an absorbent article after or at, e.g., an urination event which, thus, will reflect the status of the absorbent structure in an easily-monitored, inexpensive, and disposable way. A change in status, such as wetness or humidity, may reflect an event, such as urination or a feces event. Easily-monitored means include a remote access to the status, e.g., wetness status, without moving the user in any way and, may also, enable continuous monitoring of the status, e.g., wetness status over time.

According to an embodiment of the invention, an absorbent structure is provided, comprising at least one absorbent layer and at least one sensing device comprising a magnetoelastic film.

Further embodiments include wherein the at least one absorbent layer comprises an acquisition layer, storage layer(s), and, optionally, one or more wicking layers. The acquisition layer is intended to take up fluid and disperse said fluid to the wicking and storage layers.

In one embodiment, the absorbent structure is a disposable absorbent structure.

Another embodiment includes an absorbent structure, wherein at least one layer comprises 0–100% superabsorbent material.

In further embodiments, the layer may comprise 0–95%, 20–100%, 0–30%, 20–90%, or 30–40% superabsorbent material.

An Absorbent Structure to be Used in a Diaper Type Product or Bed Protector

One embodiment of the invention includes an absorbent structure, wherein the absorbent layer comprises at least one acquisition layer and at least one storage layer. Such an absorbent structure may be incorporated in a diaper, pants-type diaper, incontinence garment, sanitary napkin and similar product.

Figure 1B:
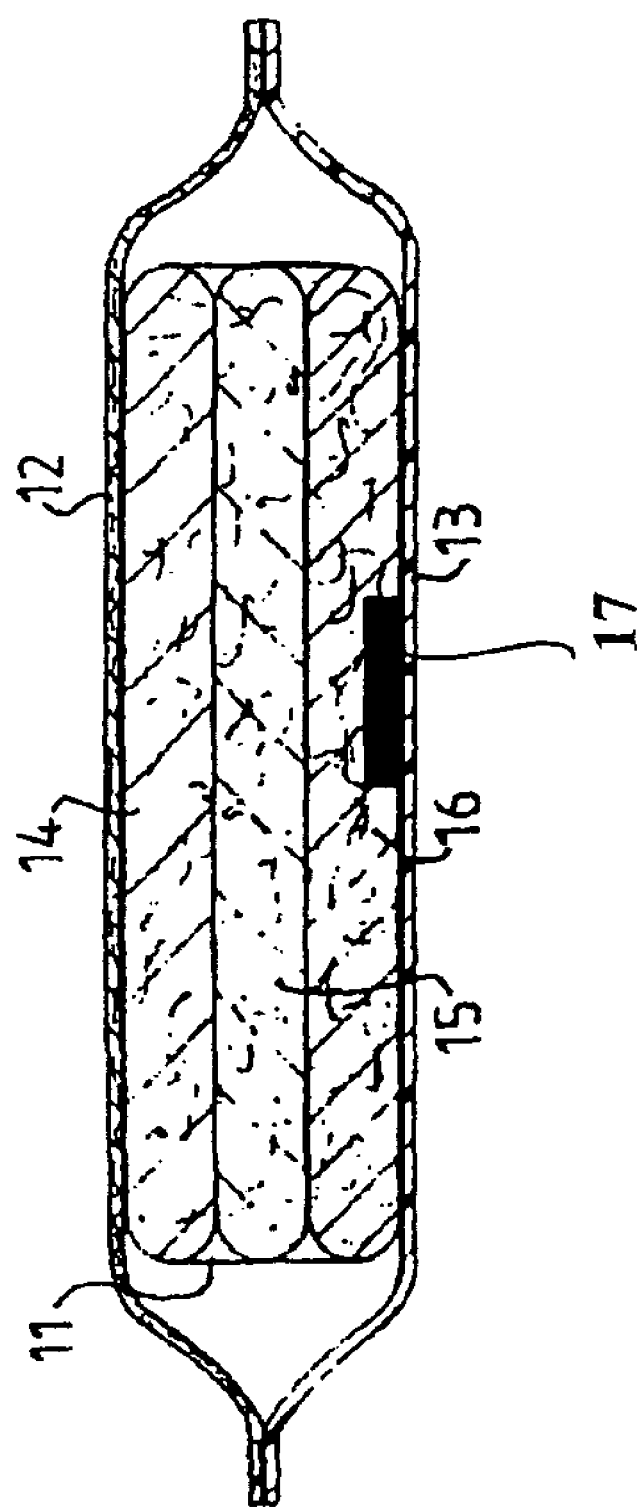

FIGS. 1A and 1B show two embodiments of an absorbent structure 11 according to the invention, suitable for an absorbent article, such as a diaper. The absorbent structure 11 is, in a conventional manner, enclosed between a fluid-permeable layer 12 which may comprise a soft non-woven material, a perforated plastic film or the like and is intended to lie proximal to the wearer when used, and a fluid-impermeable bottom sheet 13. The sheets 12 and 13 have parts, which may extend beyond the absorbent body 11. The sheets are joined together at these protruding parts. The bottom sheet 13 is comprised of a suitable plastic material, for instance polyethylene, e.g., in a laminate, a laminate between a non-woven and polypropylene, a laminate between a polyolefin and a non-woven. It may also be filled with an organic filler. It will be understood, however, that other known materials may be used for the top and bottom sheets within the scope of the invention.

The absorbent structure is comprised of two or more layers, an upper acquisition layer 14, one or more wicking layers 15, and one or more storage layers 16. The layers may be comprised of conventional cellulose fiber material. The purpose of the acquisition layer is to rapidly receive a quantity of a fluid or solid, or mixture thereof, body waste or body exudates, such as urine, feces, blood, menstruation blood, fluid matter from wounds and sores, rinsing fluid and saliva. The fluid may be loosely held in the fiber structure and quickly drained therefrom. The acquisition layer comprises dry-formed and wet-formed material in accordance with an embodiment of the invention and comprises an open structure of low density and may contain 0–30% superabsorbent material (SAP). The SAP in the acquisition layer 14 will preferably have a high gel strength, so that an open three-dimensional fiber structure will be retained in this layer after becoming wet. A suitable density range for the acquisition layer 14 is 0.30–1.0 $g/cm^3$. A suitable weight per unit area range for the acquisition layer 14 is 20–1200 $g/m^2$.

The main purpose of the wicking layer is to transport the fluid received in the acquisition layer 14 efficiently to the storage layer 16, located beneath the wicking layer 15 and the storage layer 16, to ensure that the greatest part of the storage layer 16 is utilized for absorption purposes. The wicking layer therefore preferably has a relatively low superabsorbent content. A suitable superabsorbent content, in the case of the wicking layer 15, may be 0–20% while a suitable density range may be 0.18–1.0 $g/cm^3$. A suitable weight per unit area range for the wicking layer 15 may be 50–1500 $g/m^2$.

The purpose of the storage layer 16 is to absorb and bind the fluid, which is dispersed to the storage layer 16 through the wicking layer 15. The storage layer 16 may therefore have a high density. Suitable density values may be 0.18–1.0 $g/cm^3$, while a suitable superabsorbent content may be 20–100%. In still a further embodiment, a suitable superabsorbent content may be 30–40%. A suitable weight per unit area range in the case of the storage layer 16 is 100–1500 $g/m^2$.

The wicking layer 15 and the storage layer 16 may optionally be combined to form a single layer. In this case, the single layer will have a high superabsorbent content and a high density. Suitable density values may be 0.125–1.0 $g/cm^3$, while a suitable superabsorbent content may be 20–90%. A suitable weight per unit area range in the case of a combined wicking and storage layer is 100–2000 $g/m^2$.

When the wicking layer 15 and the storage layer 16 are combined, the superabsorbent content of the layer can be varied throughout the product, so as to obtain a superabsorbent gradient on the depth, length, and/or the breadth direction of the product.

The absorbent structure may comprise one layer or several layers, such as two, three, or more layers.

The various layers may have different forms and sizes. Normally, the absorbent structure is combined with some form of elastification in, e.g., the crotch region of the product if a diaper, in order to improve product efficiency.

According to an embodiment of the invention, an absorbent structure comprises at least one absorbent layer and at least one sensing device comprising a magnetoelastic film 17. In FIGS. 1A and 1B, the position of the at least one sensing device 17 is shown. In the two embodiments shown, the sensors are placed at different depths in the absorbent structure. Other positions and number of sensors are contemplated within the scope of the invention and are further discussed below.

An Absorbent Structure to be Used in a Bed Protector, Wipe, Towel or Tissue

One embodiment according to the invention is an absorbent structure, wherein the at least one absorbent layer comprises at least one drying layer, and wherein the layer optionally comprises a plurality of individual sheets and bonding means for joining said individual sheets. The plurality of sheets allows production of, e.g., wipes, towels, bed protectors and tissue of a correct, i.e., desired, thickness that may differ from case to case due to different specific usage.

Figure 9:
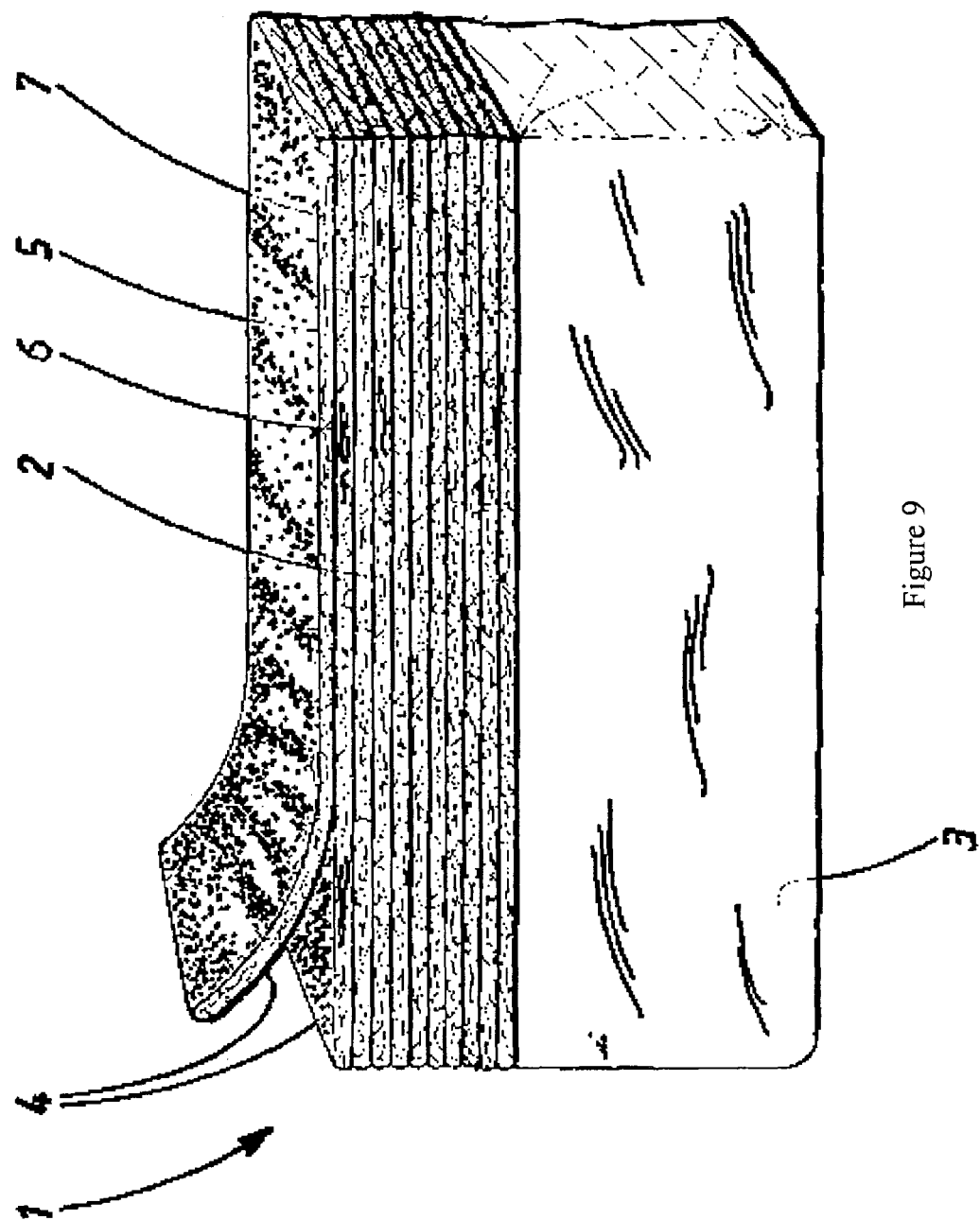
FIG. 9 shows a wipe with a plurality of individual sheets.

FIG. 9 shows an absorbing structure according to an embodiment of the invention comprising at least one sensing device detecting wetness, wherein the at least one absorbent layer comprises at least one drying layer. The figure shows a fabric for removing undesirable matter from an object by wiping, wherein the fabric comprises an absorbing structure according to an embodiment of the invention with a plurality of individual sheets, and bonding means for joining said individual sheets together.

The fabric may be a wipe for domestic or commercial uses, or for industrial or hygienic applications. Furthermore, the fabric may be oil wipes useful for wiping oils, solvent wipes useful for solvent cleaning, wet wipes useful for wet wiping, or any other wipe suitable for hygienic or household applications or suitable for removing any undesirable matter.

The wipe suitable for hygienic or household applications may be, e.g., household items such as hygienic wipes, kitchen towels, napkins, or industrial wipes.

The undesirable matter may be any fluid, e.g., domestic or industrial spills, high viscosity liquids, water, oil, solvents, chemicals or similar, any particles, any dust, any dirt, e.g., grease, stain or grime, or similar, or any kind of household dirt.

The object may be any object needing removal of undesirable matter, e.g., a whole body or any body part, such as hands, face, feet or the like, any part or any surface of, e.g., machines, vehicles, printing plates, tools, floors, walls, furniture, tables, or the like.

By "removing undesirable matter from an object by wiping" it is meant that undesirable matter from an object is removed by wiping, rubbing, polishing, stroking or similar, using the fabric.

Each individual sheet may comprise any suitable natural or synthetic material, e.g., of a woven or nonwoven type, tissue or the like. The sheet may be homogeneously or heterogeneously shaped of fibers described below.

The individual sheet may, for example, comprise fibers of polyamide, polyester, polypropylene, polyethylene or their co-polymers, or thermoplastic fibers, core-sheath conjugated fibers consisting of a polypropylene core and a polyethylene sheath, copolyester fibers or undrawn polypropylene fibers, or continuous filament, e.g., polyethylene terephthalate continuous filament, or, polyurethane, polyurea, cellulosic or cotton fibers, peat, or polylactides. Moreover, the individual sheet may comprise two or several of the components listed herein or any mixture thereof.

The bonding means for joining the individual sheets together may comprise, e.g., techniques from conventional ply-bonding or any conventional gluing techniques, e.g., use of hot or cold glue systems, and spot or strip gluing.

According to one embodiment of the present invention, the plurality of individual sheets may have coinciding edges and the plurality of individual sheets may be bonded together by said bonding means at said edges.

In another embodiment of the present invention, the plurality of individual sheets is bonded together by the bonding means in spots or strips.

Variants of bonding as disclosed herein may be achieved by using techniques from conventional ply-bonding or any conventional gluing techniques, e.g., use of hot or cold glue systems, and spot or strip gluing.

The individual sheets may comprise a nonwoven material wherein the nonwoven material may, e.g, be prepared by meltblowing, spunbonding or carding processes, and the nonwoven material may be further treated by, e.g., fluid injection entanglement or any other entanglement, ultra sound or embossment. The nonwoven material may be prepared from, for example, synthetic fibers, e.g., polymeric fibers or thermoplastic polymeric fibers or similar, natural fibers, e.g., wood pulp fibers, cotton fibers or linen fibers or other man made cellulose fibers such as viscose or rayon.

In a further embodiment according to the present invention, the individual sheets may comprise a tissue material, wherein said tissue material covers fibrous material based on cellulose or cellulose in combination with synthetic fibers.

The individual sheets may be heterogeneous. A sheet is said to be heterogeneous when said sheet is composed of more than one material, wherein the materials may have different characteristics. Each heterogeneous individual sheet may, e.g., comprise an absorbing layer and a liquid barrier layer, wherein the absorbing layer of any exposed individual sheet may constitute the outside of the fabric. The liquid barrier layer may be any liquid-impermeable layer and may, e.g., comprise a thermoplastic film.

FIG. 9 shows an absorbent structure 1, which comprises a plurality of individual sheets 2, and a body 3. The individual sheets 2, have coinciding edges and the coinciding edges have bonding means 4, for joining the individual sheets 2, together. Each of the individual sheets 2, comprises an absorbing layer 5, and a liquid barrier layer 6. Moreover, in FIG. 9, a single individual sheet 7, is also shown which is partly removed from said fabric 1.

According to an embodiment of the invention, at least one sensing device is placed in the absorbing structure. The sensing device may be placed in any of the at least one absorbing layers. The exact placing of the sensors depends on the particular usage of the wipe, tissue, towel or similar product, and on how the matter to be removed is absorbed, etc. Each embodiment thus may be considered individually when placing the sensors in an optimal way both in respect to the exact position of the sensor(s) and the number of sensors.

A Sensing Device Detecting Wetness and/or at Least One Biological and/or Chemical Analyte When a magnetic field is subjected to, e.g., a ferromagnetic material, the dimension of the material changes as an effect of the magnetostriction. The size of dimensional change of the material is governed by a magnetostriction constant.

When a magnetic material is excited by a magnetic field, it stores magnetic energy in a magnetoelastic mode. When the field is switched off the material shows damped oscillation with a specific frequency, the magnetoacoustic resonant frequency. These oscillations give rise to a magnetic flux that varies in time, which can be remotely detected by a pick-up coil.

Magnetostriction can be observed in many materials, for instance, in iron, nickel, cobolt, rare earth metals as well as in different alloys such as iron-nickel alloys, ferrites, e.g., spinel type ferrites ($Fe_3O_4$, $MnFe_2O_4$), silicon-iron alloys, and many other different alloys.

Further embodiments may use soft magnetic materials, alloys or mixtures thereof.

Still other embodiments may use amorphous magnetic material, alloys or mixtures thereof, due to the fact that amorphous magnetic material is very easy to magnetically saturate and show small magnetic anisotropy. In alloy amorphous magnetic material, the magnetostriction is also present and the amount of magnetostriction depends on the exact composition of the alloy. Examples of amorphous alloys are METGLASes such as $Fe_{40}Ni_{38}Mo_4B_{18}$, e.g., METGLAS 282 MB (Honeywell Amorphous Metals, Pittsburg, Pa., USA), $(FeCo)_{80}B_{20}$, $(CoNi)_{80}B_{20}$, $(FeNi)_{80}B_{20}$.

One embodiment uses METGLAS material from Honeywell (Honeywell Amorphous Metals, Pittsburg, Pa., USA) as the magnetoelastic material, such as METGLAS 2826 MB.

Figure 4:
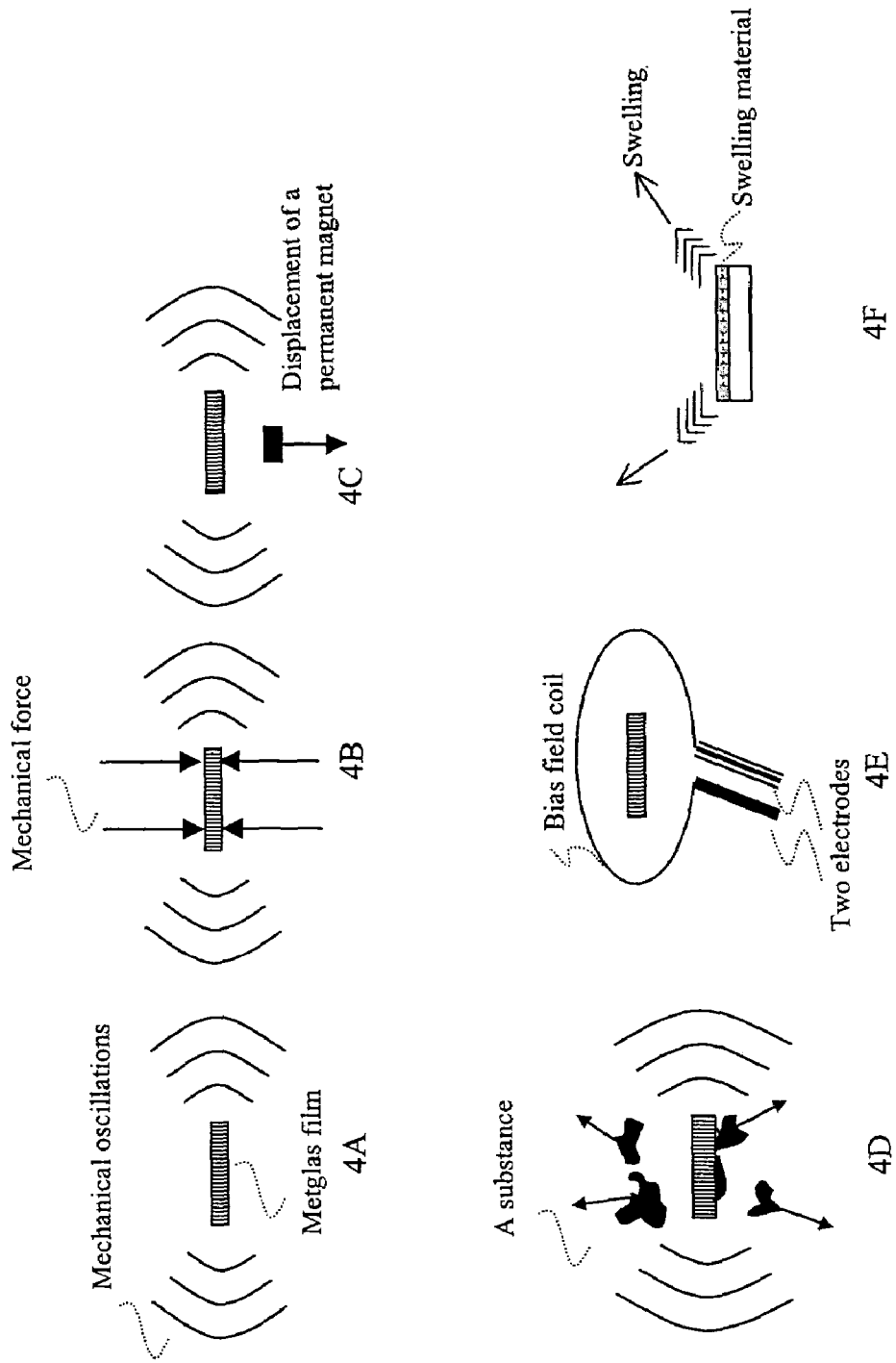
FIGS. 4A–F show five different embodiments for a sensor detecting wetness and/or at least one biological and/or chemical analyte using the magnetic METGLAS film.

One way of further enhancing the magnetostrictive effect is to include a magnetic bias field. FIG. 4E shows one embodiment with such a bias field with two electrodes included. The two electrodes in FIG. 4E is of Cu and Al, respectively. In one embodiment of the invention, such a magnetic bias field is included. A magnetic bias field has an optimal magnetic bias field, giving an optimal magnetoacoustic effect, and further giving an optimal signal from the magnetoacoustic effect (Grimes et al., Sensors and Accutators, B71:112–117, 2000). In one embodiment, the magnetic bias field is generated by a permanent magnetic film, placed in connection with the magnetoelastic film.

According to an embodiment of the invention, the absorbent structure includes at least one sensing device comprising a magnetoelastic film. Suitable magnetoelastic films may be any film with a non-zero magnetostriction and a high magnetoelastic coupling, such as an iron-nickel alloy, rare earths metals, ferrites, many different alloys and mixtures thereof, as described above. The film is intended to mean a film with a thickness of about 0.01–1000 µm, such as 0.01–200 µm, 5–100 µm, or 0.01–100 µm. Also, the thickness of the film may be much less than the width and the length of the film.

The magnetoelastic material could be used as sensors for changes in environmental properties as long as the magnetoacoustic resonant frequency changes when the environmental properties change. Changes in environmental properties include changes in mass, which is achieved by the binding of a chemical analyte such as water, a liquid, humidity or moisture, or a bioanalyte such as proteins, hormones, microorganisms (e.g., pathogenic and nonpathogenic bacteria, viruses, fungi, and parasites such as protazoans), glucose, bacterial toxins, nutritional markers, DNA, RNA, mammalian cells, such as blood cells, (e.g., lymphocytes) as further described below.

According to an embodiment of the invention, a magnetic field is applied to the magnetoelastic film in the absorbent structure. The amplitude of the pulsed magnetic field is preferably large enough to magnetize the material, e.g., the magnetoelastic film, to a certain amount in order to achieve a sufficiently large change in material dimensions. The specific magnetic fields may therefore be optimized for each magnetostrictive material chosen.

Further embodiments include where a pulsed magnetic field or a pulsed sinewave magnetic field is applied to the magnetoelastic film in the absorbent structure according to an embodiment of the invention. It will then be possible to detect a characteristic resonant frequency, i.e., the magnetoacoustic effect, between the magnetic pulses.

In different embodiments, the pulse frequencies are about 10–1000 Hz.

In further embodiments, the pulse frequencies are about 50–700 Hz.

The duty cycles of the pulses may be about 1–90%. Further embodiments include wherein the duty cycles are 10–50%.

In a specific embodiment, the magnetic field is a pulsed sinewave field. Such sinewaves may be about 50–60 kHz.

In one embodiment using METGLAS material from Honeywell as the magnetoelastic material, a magnetic field amplitude of the pulsing field may be about 0.05–0.1 mT.

In still other embodiments using the METGLAS material from Honeywell, the magnetic bias field is about 0.5–1 mT.

In other embodiments, the excitation frequency is swept across the resonance frequency to determine a frequency shift and Q-value changes, where $Q=F/(\Delta F)$, due to absorption of liquid, humidity or moisture, e.g., urine, or at least one biological and/or chemical analyte, or desorption of surface coating of the magnetoelastic film, such as the METGLAS film.

In a further embodiment, a thin ribbon of a magnetoelastic material is used. The magnetoacoustic resonant frequency for, e.g., a thin ribbon of a magnetoelastic material, is inversely proportional to the length of the ribbon. Thus, it is possible to achieve different resonant frequencies in one sensing device.

In order to detect changes in the resonant frequency, herein the magnetoacoustic effect, the sensor is preferably designed to measure correct mass changes. The sensor may then be coated with a polymer or other materials that interact with the wetness, e.g., moisture, liquid or humidity, resulting in a change in the magnetoacoustic oscillations, thus permitting detection.

One way of doing this is by coating the magnetoelastic film with a mass-changing material, or a material that may change its properties, in such a way that it affects the mass of the sensing device. This may be achieved in different ways, e.g., by gaining weight through binding a liquid, or by losing weight by, e.g., dissolving as shown in FIG. 4D. This process, as well as suitable materials for achieving this, is described in detail below.

Different Sensor Embodiments

Different embodiments of the sensor are contemplated.

One embodiment comprises a sensor that may be packaged or encapsulated accurately, not to be exposed to, e.g., mechanical pressure that may affect the resonant frequency. In such embodiments, the sensor may be packaged in a way that the wetness and/or at least one biological and/or chemical analyte found in body waste or body exudate to be detected, such as a liquid, can penetrate through the package into the magnetoelastic sensor, e.g., via pores, slots or holes, in the package material. Suitable encapsulation include encapsulations in the form of tags such as the commercially available tags from, e.g., Sensomatic, or a similar product. Thus, the encapsulations are designed or chosen in each case by the skilled man in the art to fit a specific embodiment.

In specific embodiments, mechanical pressure may correlate to the amount of analyte to be detected, e.g., wetness, humidity, or moisture and/or at least one biological and/or chemical analyte. Such embodiments may include wherein the package around the sensor is designed to allow liquid to penetrate into a region where there is an absorbing material, e.g., SAP together with magnetoelastic sensor. There may then be a mechanical pressure on the sensor correlating to the amount of, e.g., a liquid, such as urine, and/or at least one biological and/or chemical analyte that prevents or decreases oscillation. The embodiment is shown in FIG. 4B.

In another embodiment, a permanent magnet is included in the sensing device as shown in FIG. 4C. Thus, when the absorbent material swells, due to uptake of a liquid, such as urine, humidity or moisture thereof, the absorbing material pushes the permanent magnet closer or away from the magneto elastic sensor which will the change the magnetic field. Such a change in the DC magnetic field on the sensor affects the magnetoacoustic oscillations and correlates to the amount of liquid, such as urine, humidity or moisture absorbed.

Further embodiments involving a coating are described in detail below.

Figure 2:
FIG. 2 shows a magnetoelastic film, an excitation coil and a pick up coil. The magnetoelastic film is magnetized by the excitation coil with a pulsed magnetic field. The magnetic film becomes magnetized and the response from the film is detected by the pick-up coil.
Figure 2:
Figure 2:
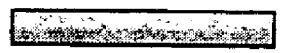

FIG. 2 illustrates how detection from the magnetoacoustic effect may be carried out by using one excitation coil that magnetizes the magnetic material and one pick-up coil that detects the response from the material.

Figure 3:
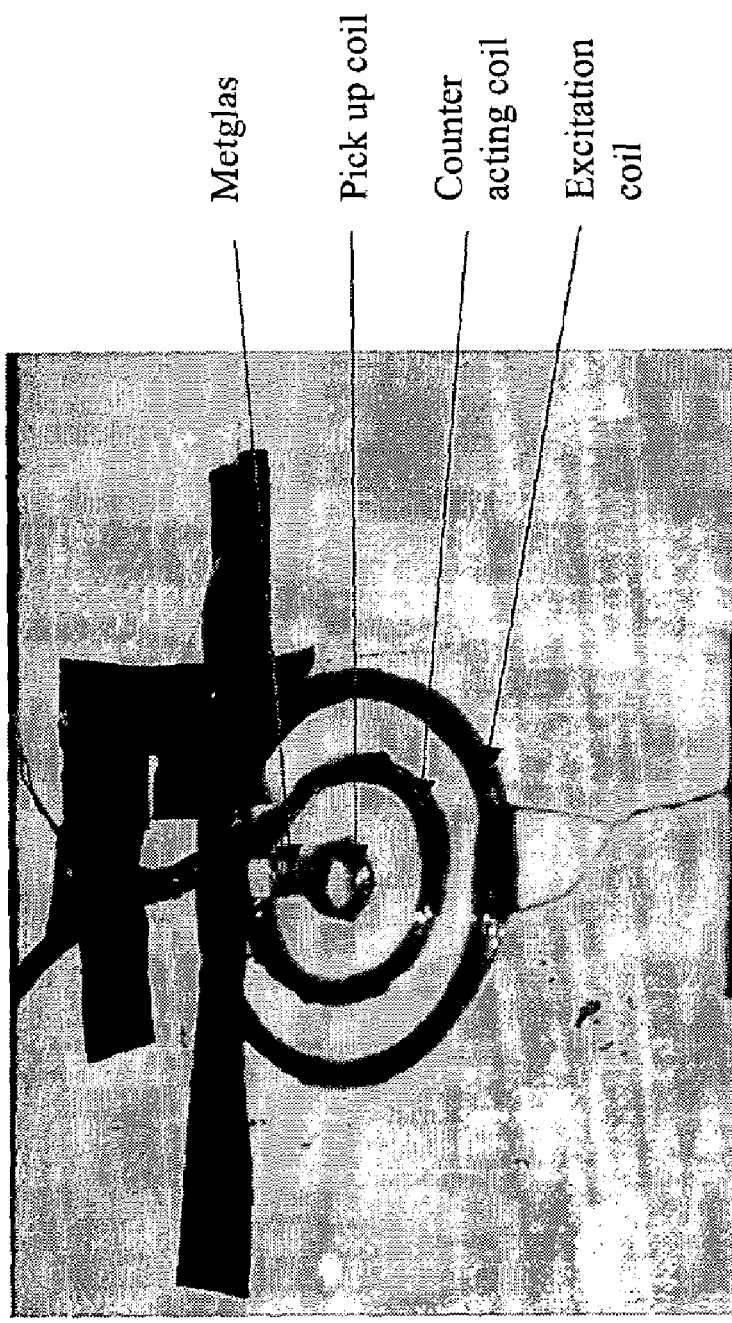
FIG. 3 shows the experimental set-up for detecting the magnetoacoustic effect. The outer coil is the excitation coil. The inner coil is the pick up coil positioned around the METGLAS film. The coil in the middle is used to counteract the field from the excitation coil.

In FIG. 3, the same is shown as in FIG. 2, but in an experimental set-up for detecting the magnetoacoustic effect. In FIG. 3, the outer coil is the excitation coil. The inner coil is the pick-up coil positioned around the METGLAS film. The coil in the middle is used to counteract the field from the excitation coil, due to this experimental set up. The position of the excitation coil and the pick up coil is further described below.

In different embodiments according to the invention, the absorbent structure comprises at least one sensing device. Due to the different sizes and shapes of such products, the number of sensing devices may differ accordingly in different embodiments. Examples may be 1, 2, 3, 4, 5, 6, 7, 8, 9, 10, 11, 12, 13, 14, 15, 20, 30, 40, or 50 sensing device(s).

The actual position of the sensor may also vary, due to different absorption patterns of body fluids, body waste or body exudates, e.g., urine, feces, blood, menstruation blood, fluid matters from wounds and sores, rinsing fluid and saliva. Also, different types of absorbent structures and absorbent articles give rise to different types of absorption patterns, due to the different preferred thicknesses of the absorbent articles and different wetting properties of the specific embodiment, which may be considered when placing the sensors in the absorbent structures and absorbent articles.

Different embodiments of the invention shown in the figures and the text below exemplify the invention showing sensors placed in the absorbing product. It will be understood that the invention is not limited to the illustrated or described exemplifying embodiments, e.g., with regard to the actual number of sensing devices, and how and the at least one sensing device is positioned.

The Hand Held Unit

The excitation coil for applying a magnetic field, which may be a pulsed magnetic field or a pulsed sinewave field, and the pick up coil that collects the produced signal, i.e., the magnetoacoustic effect, may be located in a hand held unit. In one embodiment, the hand held unit comprises both the excitation coil and the pick-up coil.

In a further embodiment, the same coil may be used both as an excitation and pick-up coil.

Figure 5:
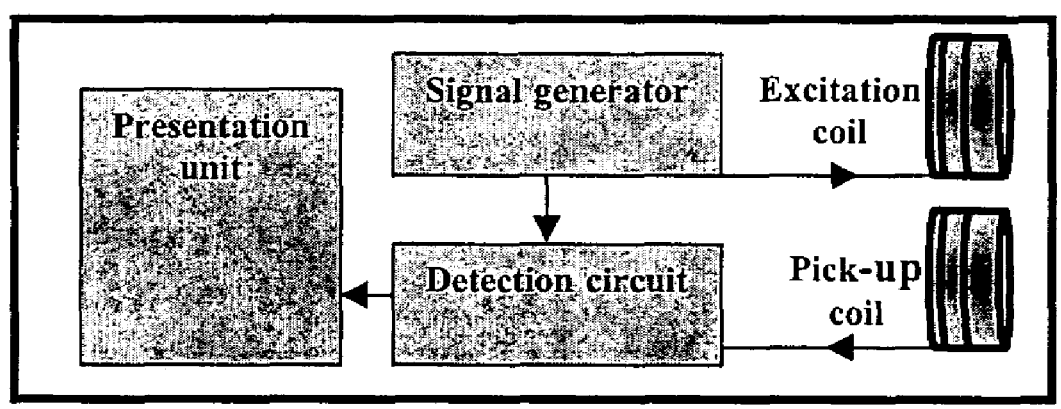
FIG. 5 shows a drawing of the handheld unit that may be used to excite the magnetoelastic film, to detect the response from the film, and to present the result for the user. It contains a signal generator that generates signals that are sent to the excitation coil and a detection circuit that receives and detects the signals from the pick-up coil. The presentation unit presents the result for the user in a proper way.

In FIG. 5, a schematic view of a hand held unit, that may be used to excite the magnetoelastic film, to detect the response from the film and to present the result for the user, is shown. It contains a signal generator that generates and sends signals to the excitation coil and a detection circuit that receives and detects the signals from the pick-up coil. The presentation unit presents the result for the user in a proper way. The signal generator is connected to the detection circuit so that the detection circuit "knows" when a signal is sent to the excitation coil. Furthermore, the handheld unit may be designed to minimize the magnetic coupling between the excitation coil and the pick-up coil. The position of the pick-up coil with respect to the excitation coil may be optimized for maximum signal from the film and minimal signal due to the magnetic field from the excitation coil. The pick-up coil may be oriented 90 degrees with respect to the excitation coil and positioned in the excitation coil. There may be a signal noise in the pick-up coil due to the magnetic field change in the excitation coil but this is handled by proper signal processing.

In further embodiments, the excitation coil and the pick-up coil may be separated in different units.

An Absorbent Structure with a Wetness Sensing Device

The absorbent structure described above may, in a specific embodiment, include a magnetoelastic film coated with a wetness sensitive material. The coating may be directly on the magnetoelastic film, or indirectly, having other layers in between the magnetoelastic film and the polymer.

In specific embodiments, the wetness sensitive material may absorb the wetness, such as urine, and in such cases, change the mass of the sensing device, which will increase or decrease the total weight of the sensor. This change in mass will either increase or decrease the resonant frequency, e.g., the magnetoacoustic effect, and is thus measurable and further correlates to the amount of wetness, such as urine, absorbed to the sensing device.

In FIGS. 4A–F, different embodiments of the sensing device are shown. FIG. 4A shows the mechanical oscillations from the METGLAS film, that may change differently in different embodiments dependent on how the wetness is detected. The different embodiments are further discussed below in detail.

Referring to FIG. 5, the change in mass will be picked up as a change in the magnetoacoustic frequency due to a mass-change in the magnetoelastic film by a pick-up coil, and the signal further detected by a detection circuit that detects the signal from the pick-up coil.

In FIG. 4B a further embodiment is shown. In this embodiment, the package around the sensor may be designed allowing liquid to penetrate into a region where there is an absorbing material, e.g. SAP, together with the magnetoelastic sensor as shown in FIG. 4B. The SAP will then exert a mechanical pressure on the sensor when absorbing liquid, moisture or humidity. The pressure will correlate to the amount of, e.g., liquid or moisture, that will completely or partially dampen said oscillation. Thus, a decrease in the magnetoacoustic effect will be detected when the oscillations are dampened.

Still another embodiment is shown in FIG. 4C. In this embodiment, the absorbing material, such as SAP, pushes a permanent magnet closer or further away from the magnetoelastic sensor when wet or becoming wet. This will change the magnetic field. Such a change in the DC magnetic field on the sensor affects the magnetoacoustic oscillations. Thus, an increase or decrease in the magnetoacoustic effect may be detected in the embodiment shown in FIG. 4C, or a similar embodiment detecting such a change in the oscillation.

In FIG. 4D, a further embodiment is shown. The magnetoelastic film in FIG. 4D is coated with a material, e.g., a low molecular weight compound such as NaCl, that dissolves when exposed to a liquid of moisture as shown in the figure.

This may also give rise to a mass change, thus increasing the magnetoacoustic resonance frequency.

In FIG. 4E, an embodiment of the sensing device is shown comprising a bias field coil. Such an embodiment may comprise two electrodes, made of, e.g., Cu or Al.

In FIG. 4F, an embodiment of the sensing device is shown. The magnetoelastic film in FIG. 4F is coated with a wetness-sensitive material that swells when exposed to a liquid of moisture as shown in the figure. This may also give rise to a mass change, thus increase the magnetoacoustic resonance frequency. The wetness-sensitive material is selected from the group consisting of linear and hydrophilic polymers or chemically/physically cross-linked swellable polymer gels based on polyvinyl alcohol, polyvinyl pyrrolidone, polyethylene oxide and co-polymers thereof, polyurethane, polyamides, starch and derivatives thereof, cellulose and derivatives thereof, polysaccharides, proteins, polyacrylonitrile, acrylate-based polymers, and mixtures thereof.

In still another embodiment, sensors comprising magnetoelastic films of different lengths, which will give different resonance frequencies, may be placed at different positions in the product. This will allow for a readout locating the precise position or part of the product that has become wet.

An Absorbent Structure with a Sensing Device Sensing Biological and/or Chemical Analytes The absorbent structure described above may in a further embodiment include a magnetoelastic film, which is directly coated or indirectly coated, i.e., with other layers such as suitable coupling layers in between, with at least one detector molecule onto the sensing device, thus to be adapted to detect a target biological and/or chemical analyte in body waste, body exudate, or the user or wearer's skin.

Biological analytes or bio-analytes are, e.g., biologically derived materials such as an enzyme or sequence of enzymes; an antibody; a membrane receptor protein; DNA; RNA; proteins; peptides; organelles; a natural or synthetic cell membrane; an intact or partially viable or nonviable bacterial, plant, or animal cell; plant or animal (particularly mammalian) tissue; or any other biologically derived molecule. Further examples are given below.

The absorbent structure of an embodiment of the invention may also include at least one sensing device sensing a biological and/or chemical analyte, which is an enzyme; an antibody; a nucleic acid such as DNA or RNA; a protein such as a soluble protein or a membrane protein; a peptide such as an oligopeptide or polypeptide; parts of a cell membrane or capsid such as a bacterial or mammalian cell membrane, or a virus capsid; a lipid; a carbohydrate; a lectin, or mixtures thereof.

Further embodiments include, wherein the at least one sensing device targets a biological and/or chemical analyte, which is a pathogenic bacteria, non-pathogenic bacteria (e.g., colonic bacteria), viruses, parasites, bacterial toxins, fungi, enzymes, proteins, peptides, mammalian blood cells (e.g., red and white blood cells), hormones, mammalian tissue (including human), blood components (e.g., blood glucose), and mixtures thereof. In other embodiments, the at least one sensing device targets biological and/or chemical analytes in urine, such as glucose, ketones, bilirubin, urobilinogen, etc.

Still even further embodiments include wherein the bacteria, pathogenic or not, is *Escherichia coli, Salmonella typhi, Salmonella paratyphi, Salmonella enteriditid, Salmonella thyphimurium, Salmonella heidelberg, Staphylococcus aureus, Shigella sonnei, Shigella flexneri, Shigella boydii, Shigella dysenteriae, Vibrio cholerae, Mycobacterium tuberculosis, Yersina enterocolitica, Aeromonas hydrophila, Plesmonas shigelloides, Campylobacter jejuni, Campylobacter coli, Bacteroides fragilis, Clostridia septicum, Clostridia perfringens, Clostridia botulinum, Clostridia difficile*, or a mixture thereof.

Other embodiments of the sensing device include the sensing of a chemical compound or analyte such as a health marker or nutritional marker. Health markers or nutritional markers may reflect the nutritional status of the wearer.

Nutritional markers include markers for, e.g., metabolic efficiency, nutrient deficiencies, nutrient absorption or malabsorption, food and drink intake, food allergies (e.g., to peanuts), food intolerance (e.g., lactose or gluten intolerance), colonic bacteria ecology (e.g., beneficial bacterias such as bifidobacteria and lactobacillus), and total energy balance.

Health markers may include chemical analytes such as heavy metals (e.g., lead, mercury, etc.), radioactive substances (e.g., cesium, strontium, uranium, etc.), fats, enzymes, endogenous secretions, protein matter (e.g., blood casts), mucous and microorganisms, as described above, that may be related to various health issues such as infection, diarrhea, gastrointestinal distress of disease, or poisoning. Heavy metals, especially in certain developing countires and in older and/or less affluent areas of developed countries, are a serious health risk. For example, lead and mercury poisoning may occur upon the ingestion of heavy metals from environmental sources (e.g., from lead paint, unregulated heavy metal industries, etc.) and can be fatal. More commonly, low-level poisoning by these and other heavy metals results in retarded intellectual and/or physical development, especially in children, that may occur over a long time and have lasting effects on the individual.

Other examples of nutritional markers include calcium, vitamins (e.g., thiamine, riboflavin, niacin, biotin, folic acid, pantothenic acid, ascorbic acid, vitamin E, etc.), electrolytes (e.g., sodium, potassium, chlorine, bicarbonate, etc.), fats, fatty acids (long and short chain), soaps (e.g., calcium palmitate), amino acids, enzymes (e.g., lactose, amylase, lipase, trypson, etc.), bile acids and salts thereof, steroids, and carbohydrates. For example, calcium malabsorption is important in that it may lead to a long-term bone mass deficiency.

Examples 8–11 demonstrate the use of METGLAS as a biosensor, e.g., a biosensing device using wholly or partially physiosorbed detector molecules using, e.g., a cationic polymer such as polyethyleneimine (PEI, from Sigma Aldrich), a colloidal suspense such as polybead polystyrene (PS) microspheres (from Scientific Polymer Products), or a hydrophobic polymer such as polystyrene (from Scientific Polymer Products). The experiments show the use of coated METGLAS for detection of bacteria and blood cells, e.g., lymphocytes.

Suitable detector molecules to be attached or coated directly or indirectly onto the sensing device, e.g., onto the METGLAS surface. Sensing bioanalytes or chemical analytes may include any biorecognition element and are further exemplified by carbohydrates, antibodies or parts thereof, synthetic antibodies or parts thereof, enzymes, lectins, DNA, RNA, cells, and/or cell membranes or any other molecules with a binding capacity for a defined bioanalyte or chemical analyte.

It will be obvious to one skilled in the art that any suitable means of applying the detector molecule besides physiosorption onto the METGLAS surface may be appropriate for other applications. For example, it may be desirable to chemically bind the detector molecule, directly or indirectly, to the surface using any one of a variety of common crosslinker molecules including but not limited to glutaraldehye, N-hydroxysuccinimide, carbodidimides.

For especially high precision applications, it may be desirable to use the technique of making self-assembled monolayers (SAMS) on the detector surface as a means for coating detector molecules. SAMS can be made by a number of different techniques which are familiar to those skilled in the art. One preferred method of making a SAM is to first deposit a monolayer of an element such as gold, copper, silver, lead, platinum, or carbon on the sensing surface of the METGLAS film, gold is the most preferred element for use in coating the film.

By immersing the coated METGLAS film in a solution of organic molecules containing thiol, dithiol, nitril, carboxylic acid, amine, or silane functional groups, a SAM layer will be spontaneously formed on the coated surface. Long chain alkane or aromatic molecules with thiol functional groups are especially preferred to form stable densely packed monolayers on gold surfaces. It is also possible to form a SAM directly on the METGLAS surface without first coating with a monolayer of gold or other elements. Alkane phosphates and phosphonates have been shown to form SAMS on transition metal oxide surfaces and thus would be suitable for forming SAMS on iron, cobalt, or niobium-based METGLASes. Other methods known in the art can also be used for forming the SAM.

Once the SAM has been formed, the detector molecule can be easily attached to the monolayer by a number of means known in the art. The detector molecule can be physically absorbed onto the monolayer. The detector can also be covalently attached to the monolayer molecules using a second functional group located on the individual molecules, including, but not limited to, succinimide, amino, carboxyl, and aldehyde groups. Finally, the detector can be immobilized by use of detector molecules and of monolayer molecules which are both labeled with the appropriate half of a receptor-ligand pair. The streptavidin-biotin system is especially favored for use in positioning detector molecules on the sensor.

If so desired, the non-binding surfaces of the sensor can be blocked to prevent non-specific binding of the analyte molecule to the surface. Such blocking can be achieved in a number of ways, including, but not limited to, adsorption of a globular protein such as albumin or casein onto the surface, or by covalently binding a blocking polymer to non-binding sites of the SAM. Medium or short chain PEG molecules are a preferred blocking agent.

Absorbent Articles

The absorbent structure according to the invention may be included in different types of absorbent articles. In various embodiments, the structure forms part of a disposable absorbent article, and the article is an absorbent article such as a diaper, a pants-type diaper, incontinence garment, sanitary napkin, wipe, towel, tissue, bed protector, wound or sore dressing, or similar product comprising the absorbent structure according to the invention, a fluid-permeable top sheet, and an essentially fluid-impermeable bottom sheet.

Without limiting the invention, various absorbent articles are further exemplified below.

A Diaper

Figure 6A:
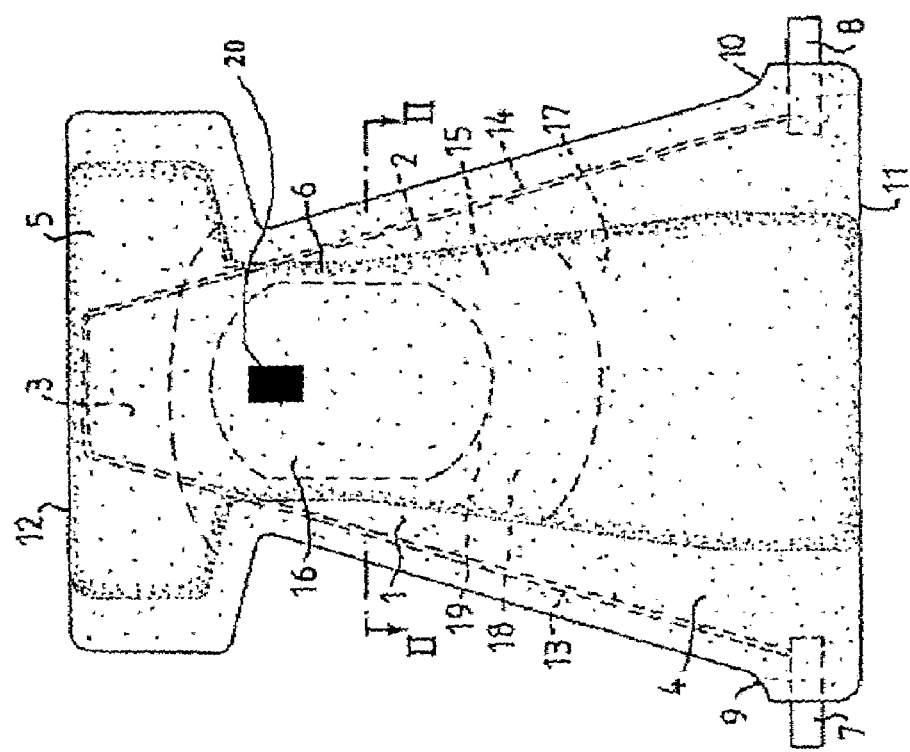
FIGS. 6A–C show an embodiment of a diaper comprising the absorbent structure according to the invention, a front-part, a back-part, a crotch-part between the front and back-parts.
Figure 6B:
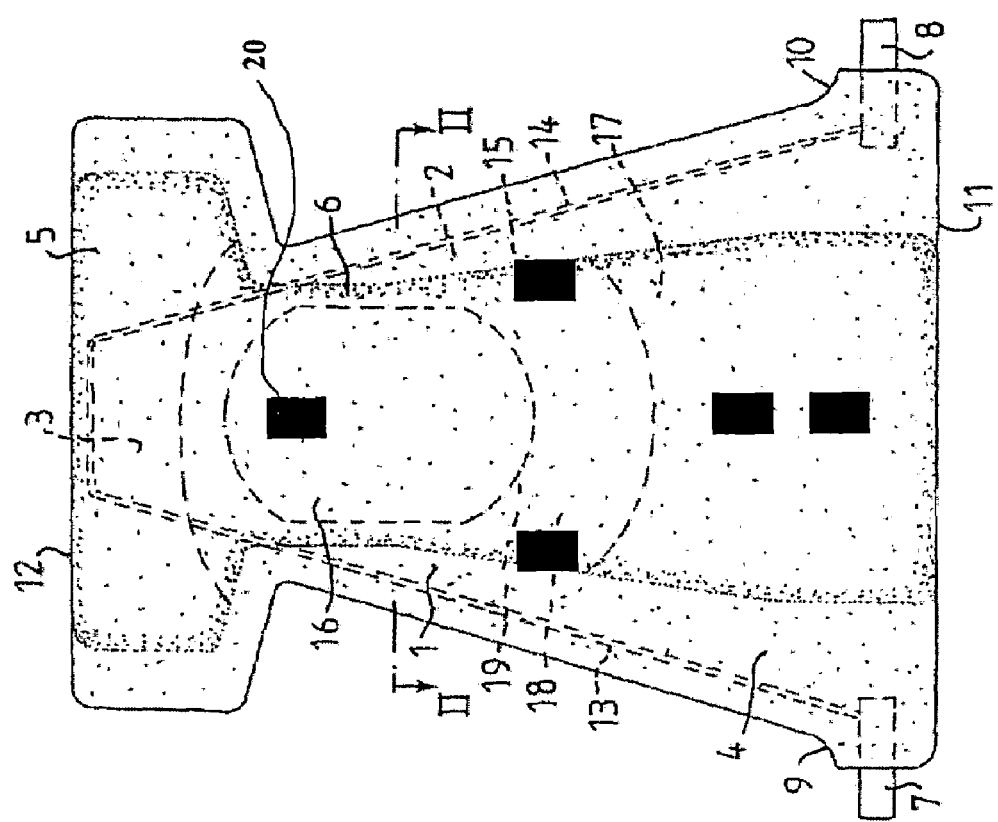
Figure 6C:
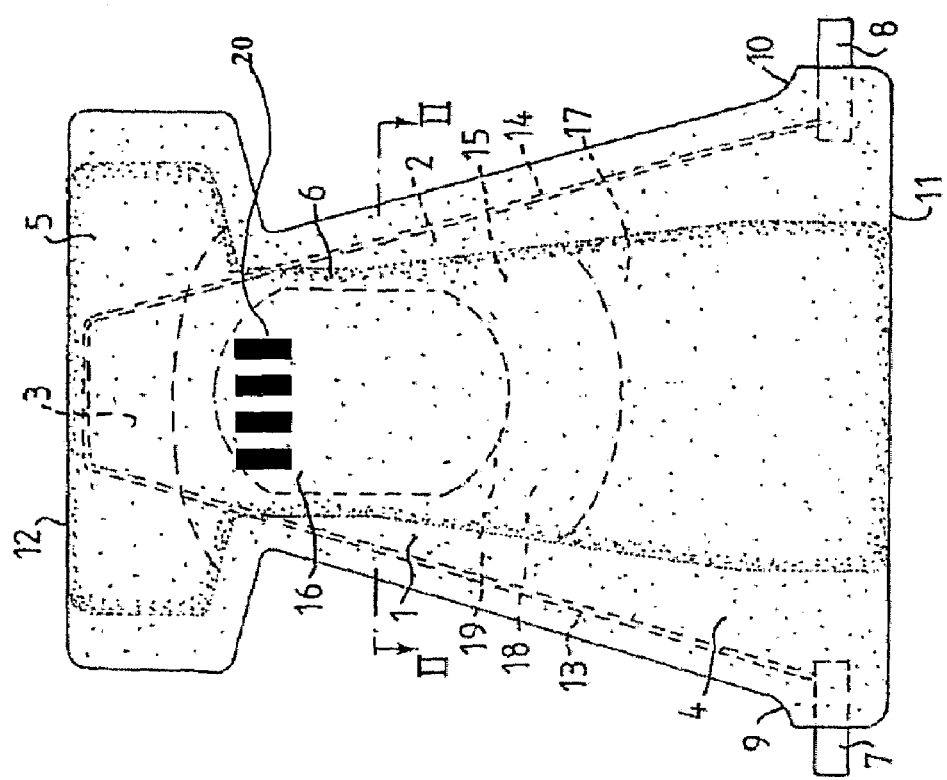

FIGS. 6A–C show different embodiments of the invention, e.g., a diaper comprising the absorbent structure according to the invention, a front-part, a back-part, and a crotch-part between the front and back-parts as well as at least one sensing device 20 at different positions in the diaper.

Moreover, the absorbent structure may have a front and a rear end-part, an intermediate center part, and an inner top sheet layer placed on a side which is intended to face towards the user/wearer, and an outer top sheet layer placed on the opposite side intended to face away from the user/wearer.

The diaper may, in different embodiments, be a diaper wherein the absorbent structure according to an embodiment of the invention comprises about 1, 2, 3, 4, 5, 6, 7, 8, 9, or 10 sensing device(s) 20.

In one embodiment, one sensing device 20 is included. The placement of such a sensing device 20 may be according to FIG. 6A. The placement may be different on other embodiments of a diaper, due to different, e.g., wetting profiles and wetting points of a diaper.

The wetting point is an area of the diaper surface onto where the body liquid or body waste first comes into contact. As will be understood, it is not possible in practice to establish any specific point or area in this regard, although it can be generally accepted that the body liquid or waste will be delivered to the diaper within a given, limited area thereof. In general, this area is displaced slightly towards the front of the diaper part, in the case of both male and female wearers. Since the dispersion of the liquid in the first absorbent layer, i.e. the acquisition layer, is only slight, it is sufficient for this layer to cover solely the area of the diaper in which wetting is most likely to occur. Accordingly, such aspects are analyzed and considered when placing sensoring devices in an absorbent structure, such as the diaper according to the invention.

In a further embodiment, several sensors 20, which may possess different resonance frequencies, are placed in the absorbing structure. The placement may be in the rear, in the front and on the sides of the diaper, as seen in FIG. 6B. This may allow for measurements over time, of, e.g., wetness in the whole diaper. The placement of sensors on the side may as well additionally indicate leakage of, e.g., liquid or feces, in the crotch part of the diaper.

The placements of the sensors 20 in FIGS. 6A and 6B are only to be considered as examples, and further embodiments are contemplated for the particular use and analysis to be performed. For example, if urine is to be measured, several sensors 20 may be placed in the front of the diaper as shown in FIG. 6C, thus indicating an urination event.

The diaper illustrated in FIGS. 6A–C is comprised of a liquid-permeable top sheet 1, for instance, a non-woven or perforated plastic film, a liquid-impermeable top sheet 2, for instance, a plastic film or a hydrophobic non-woven material, and an absorbent body 3 enclosed between the two layers 1, 2.

The diaper is intended to embrace the lower part of the wearer's trunk, in the manner of a pair of absorbent underpants. The diaper is provided with a back part 4 which, when the diaper is worn, will be located rearwardly on the wearer, a front part 5, which when the diaper is worn will be located forwardly on the wearer, and a narrower crotch part 6 which extends between the back part 4 and the front part 5 of the diaper and which, when the diaper is worn, is located in the crotch region of the wearer, between the thighs thereof. Fastener tabs 7, 8, are provided on the side edges 9, 10 of the back part 4 extending in the longitudinal direction of the diaper, close to the rear waist edge 11 of said diaper, so as to enable the diaper to be secured in the desired pants-like form. When the diaper is to be used, the fastened tabs 7, 8 are fastened to the outer surface of the front diaper part 5, close to the forward waist edge 12, thereby holding the diaper together around the wearer's waist.

The diaper illustrated in FIG. 6 also includes prestretched elastic devices 13, 14 which extend over the diaper in a V-shaped pattern, with the apex of the V located on the forward waist edge 12 of the diaper. The elastic devices 13, 14 may consist of any suitable material, such as elastic foam, elastic bands or covered elastic threads. For the sake of convenience, the elastic devices 13, 14 have been shown in a stretched state. However, as soon as the tension is removed, the elastic devices will contract and therewith form elastic leg openings on the diaper.

The absorbent structure 3 is comprised of mutually different layers. Nearest to the liquid permeable top sheet 1 is a thin cellulose fluff-pulp layer 15 of high critical bulk, large pore volume and low liquid-dispersion ability. By critical bulk is meant the bulk at which a cellulose body will neither collapse nor expand when becoming wet. A cellulose fluff-pulp of high critical bulk will retain an open structure of large pore volume even when wet.

Seen in a direction towards the liquid-impermeable top sheet 2, there then follows a first absorbent layer 16, which is comprised of cellulose fluff-pulp of large pore volume, high wet resilience and low liquid-dispersion ability, and a second absorbent layer 17 comprised of cellulose fluff-pulp of low pore volume, low wet resiliency and high liquid-dispersion ability. Both absorbent layers also include superabsorbent material.

The cellulose fluff-pulp layer 15 lying closest to the liquid-permeable top sheet layer 17 has a T-configuration with the cross-member of the T being located at the front diaper part 5. The first absorbent layer 16, on the other hand, has an oval shape and is located generally in the crotch part 6 of the diaper, around the so-called wetting point.

The first receiving layer, i.e. the acquisition layer, in the diaper according to the invention thus functions as a receiving area for discharged body liquid or waste.

CTMP fluff, CF fluff, wadding or foam is suitable for use in the first absorbent layer. SAP may be added in different proportions to this layer as well.

The first absorbent layer 16 may also contain between 2–30% superabsorbent material, preferably 2–15% superabsorbent material, calculated on the total dry weight of the layer in that area in which the superabsorbent material is mixed. The superabsorbent may be distributed generally uniformly in the layer, within at least one area or region thereof, and is intended to bind any liquid that remains in the layer, even when the layer has been drained by the second absorbent layer 17, which may be a wicking layer.

As mentioned previously, the superabsorbent material in the first absorbent layer should preferably have a high gel-strength, to retain an open fiber structure even when becoming wet.

The second absorbent layer 17 also contains superabsorbent material, which may be in the form of one or more layers of flakes, fibers, granules, powder or the like. The layer extends either over the whole of the absorbent layer 17 or is restricted to at least one area thereof. This area may, for instance, be slightly larger than the absorbent layer 16 and, similar to said layer, may be limited essentially to the crotch part of the diaper.

The proportion of superabsorbent included in the second absorbent layer 17 will preferably be between 2 and 60%, preferably between 19 and 50%, calculated as a fraction of the total dry weight of the layer.

The super absorbent in the second absorbent layer 17 will preferably have a high gel-strength, i.e., has the ability to swell substantially unaffected by normally occurring pressure forces, so as not to block or impede dispersion of the liquid. Characteristic of these super absorbents is that they have a high degree of cross-linking which renders them more difficult to compress in comparison with a gel that has a lower degree of cross linking.

The fluff pulp in layer 17 of the second absorbent layer may comprise substantially fluff-pulp or some other absorbent material having a high liquid-dispersion capability. Chemically produced fluff-pulps, of cellulose material, generally fulfill this. The final fibers may have a weight of 140–190 (g/m, a low degree of stiffness and low wet-stability, and a critical bulk beneath 8 $cm^3/g$ at 2.5 kPa.

The second layer 17 may also comprise a chosen fluff pulp, such as CTMP-pulp or chemical pulp.

Thus, discharged body fluid or waste is first collected in the first absorbent layer 16, which functions as a buffer, or reservoir, this layer being successively drained as the second absorbent layer 17, absorbs and disperses the liquid waste.

It will be understood that the illustrated and described diaper is merely intended to exemplify the invention and shall not be considered to limit the scope of the invention. For instance, the shape of the diaper and its construction in other respects may be varied. Similarly, the first absorbent layer 16 may fully cover the second absorbent layer. Furthermore, the thin cellulose fluff-pulp layer 15 located nearest to the liquid-permeable top sheet layer 1, may be omitted.

It should also be noted that a diaper, as used herein, is particularly used in conjunction with incontinence, especially adult incontinence, but that the invention is not limited to this particular use or any particular size or type of diaper implied thereby, but may be any diaper obvious to the person skilled in the art.

In a further embodiment, the diaper product comprising the wetness sensing device 20 is a disposable diaper.

A Pants-type Diaper

According to one embodiment of the invention, a pants-type diaper comprising the absorbent structure is disclosed. Such a pants-type diaper comprises a front-part, a back-part, a crotch-part between the front and back-parts.

Furthermore, it may comprise at least two side-closure parts which mutually join parts of the side-edges of respective front and back-parts, so that the diaper will present a waist opening and two leg openings. The absorbent structure may have a front and a rear end-part, and an intermediate center part, an inner top sheet layer placed on a side which is intended to face the towards the user/wearer, and an outer top sheet layer placed on the opposite side intended to face away from the user/wearer.

The pants-type diaper according the invention may in specific embodiments be a diaper pant, wherein the absorbent structure according to the invention comprises 1, 2, 3, 4, 5, 6, 7, 8, 9, or 10 sensing device(s).

Figure 7A:
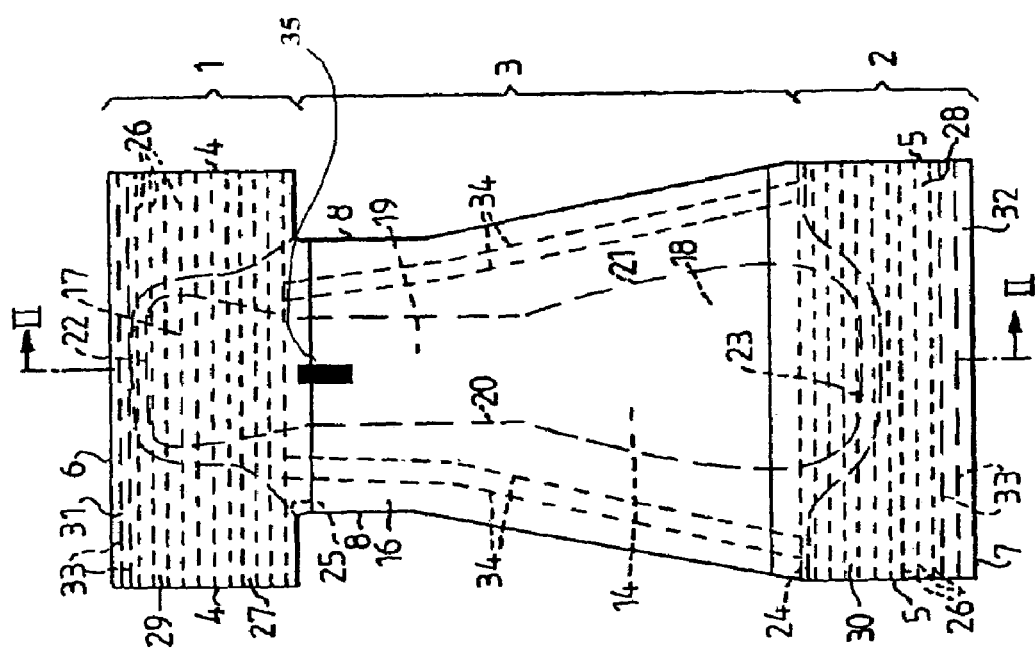
FIG. 7A is a perspective view of a simplified embodiment of a pants-type diaper in an unassembled state with one sensing device 35 placed in the absorbing structure.

In FIG. 7A, one sensing device 35 is incorporated in the pants-type diaper.

Figure 7B:
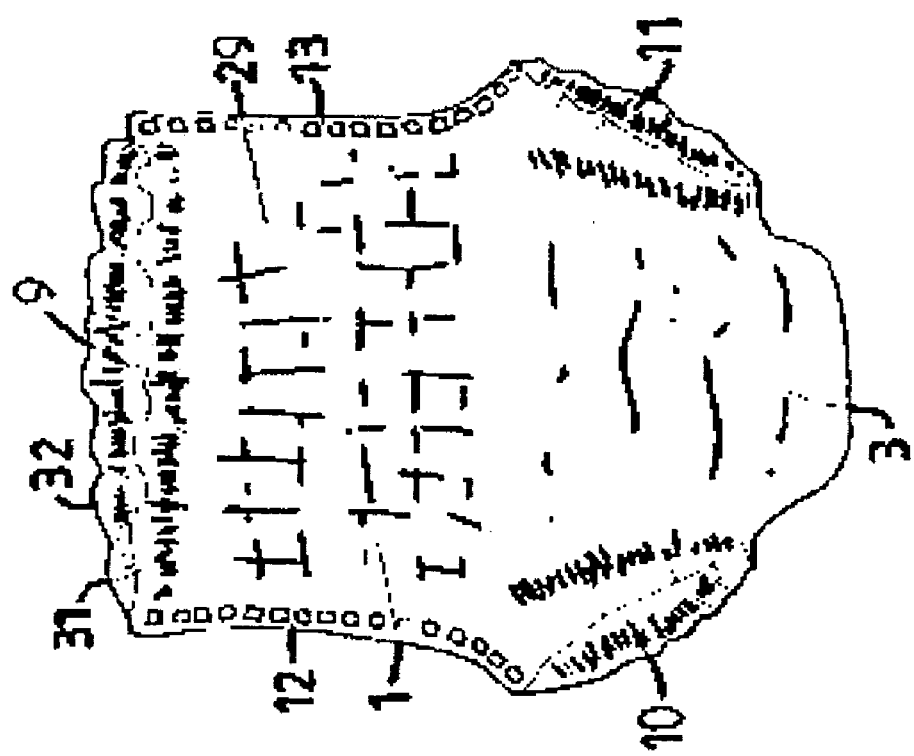
FIG. 7B is a perspective view of a simplified embodiment of a pants-type diaper, in an assembled or ready-to-wear state.
Figure 7C:
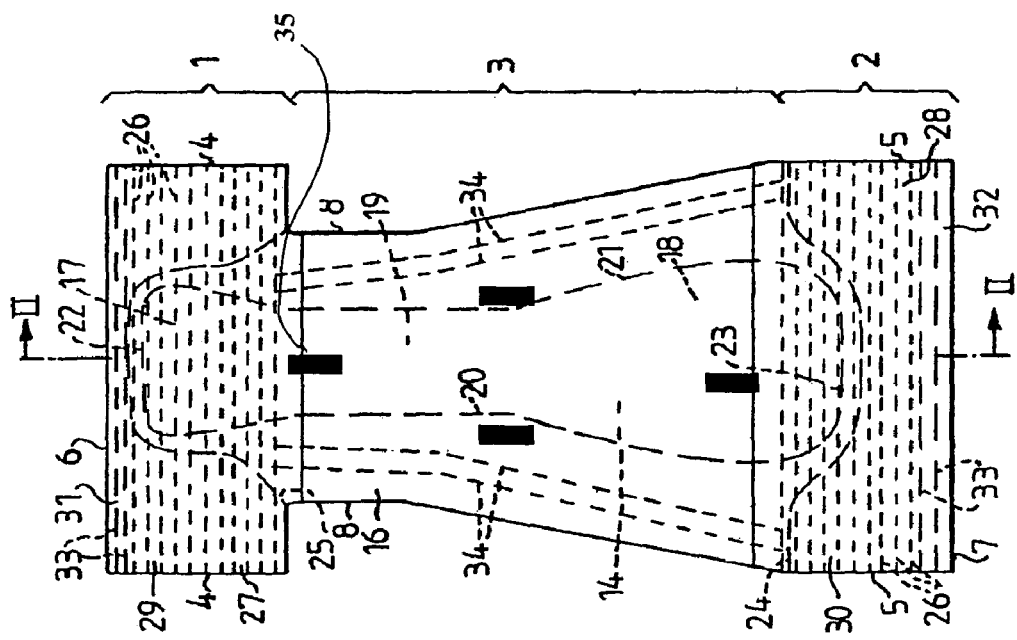
FIG. 7C shows the same as in 7A, but with four sensing devices 35 placed in the absorbing structure.

FIG. 7C shows still a further embodiment with four sensing devices 35 according to the invention. Sensors may be placed in the pants-type diaper as in the diaper described above, or in any other configuration to fit the purpose of the wetness detection of the user.

FIG. 7B is a perspective view of a simplified embodiment of a pants-type diaper, in an assembled or ready-to-wear state. FIGS. 7A and C show the same diaper in an unassembled state but with different numbers of sensing devices placed in the absorbing structure. The pants-type diaper has a waist opening 9 between respective end-edges 6, 7 of the front and the back parts, and two leg openings 10, 11 which are surrounded by respective side-edges 8 of the crotch-part. Respective side edges 4 of the front-part are joined to corresponding respective side-edges 5 of the back-part, such that the pants will present two-side closure parts 12, 13 which extend from the waist opening 9 to respective leg openings 10, 11 on respective side of the diaper. The side closures may be obtained with the aid of heat sealing, ultrasonic welding, gluing or sewing techniques or some other suitable conventional technique.

In FIGS. 7A and C, the pants-type diaper includes a front-part 1, which is intended to be placed forwardly on the wearer, a back-part 2, which is intended to be placed rearwardly on the wearer, and a crotch part 3 which is located between the front and the back parts 1, 2 and which is intended to be placed between the thighs of the wearer. No precise limits can be drawn between the respective parts and the size relationships can vary. Consequently, the pants-type diaper in FIGS. 6 and 7 is only a schematic example. Each of the front and the back parts have two side-edges 4, 5 and one end-edge 6, 7. The crotch part 3 has two side edges 8.

As will be seen in FIG. 7B, when the pants-type diaper is in its assembled or ready-to-wear state, the diaper has a waist opening 9 between respective end-edges 6, 7 of the front and the back-parts, and two leg openings 10, 11 which are surrounded by respective side-edges 8 of the crotch-part. Respective side-edges 4 of the front-part are joined to corresponding respective side-edges 5 of the back-part, such that the pants-type diaper will present two-side closure parts 12, 13 which extend from the waist opening 9 to respectively leg openings 10, 11 on respective side of the diaper.

It will be seen in FIGS. 7A and 7B that the pants-type diaper includes an elongated absorbent structure 14 according to an embodiment of the invention, which extends in the longitudinal direction of the diaper and which is enclosed between an inner top sheet layer and an outer top sheet layer 16, with the latter facing towards the viewer of FIGS. 7A and 7B. The inner top sheet layer is placed on that side of the absorbent structure 14 which faces towards the wearer in use and is liquid impermeable and comprises, e.g., non-woven material. The fibers may comprise, e.g., polyethylene, polypropylene, polyester or mixtures thereof. They may also be comprised of viscose fibers. It is also conceivable for the inner top sheet layer to comprise a perforated plastic sheet, for instance, polyethylene film or the like. The outer top sheet layer, or backing sheet, 16 is liquid-impermeable or at least hydrophobic and may, for instance, comprise a sheet of polyethylene or a non-woven material which has been coated or laminated with polyolefins, for instance, so as to become liquid-impermeable or at least hydrophobic.

The absorbent material in the absorbent structure 14 according to an embodiment of the invention, may essentially be the same as for the diaper article described above.

Another embodiment comprises cellulose fibers. The material may also include other absorbents, such as polymeric hydrocolloidal material, e.g., superabsorbents. The absorbent structure may also comprise non-absorbent material, for instance thermoplastic melt fibers, with the intention of strengthening the absorbent structure. Although the absorbent structure in FIGS. 7A–C has only a single layer it is understood that the absorbent structure may comprise more than one layer in other embodiments according to the invention.

The absorbent structure is not restricted to the shape illustrated in FIGS. 7A–C. Other shapes, such as hourglass shapes or T-shapes, are conceivable.

Different embodiments shall not be considered to be restricted to the illustrated exemplified embodiments, since several variations are conceivable within the scope of the claims. Further possible pants-type diapers to be used, are described in WO 93/17648, incorporated herein by reference.

Further embodiments include wherein the pants-type diaper is disposable.

A Tampon-like Structure

Another embodiment of the invention comprises an absorbent article such as a tampon-like structure. Such an absorbent article comprises the absorbent structure according to the invention. The tampon-like structure may be suitable for the absorption of blood, such as menstrual blood, or as a wound or sore liquid absorbing tampon-like structure. Also, similar tampon-like structures may be suitable for, e.g., absorption of saliva in the oral cavity.

In one embodiment, the structure contains 5–100% cellulose fibers mainly comprising fibers of chemothermomechanically producer pulp (CTMP) and between 0–15% superabsorbent material, calculated as a fraction of the total weight of the structure in a dry state. In further embodiments, the tampon-like structure comprises the absorbent structure according to an embodiment of the invention comprising 1, 2, 3, 4, 5, 6, 7, 8, 9, or 10 sensing device(s).

Figure 8:
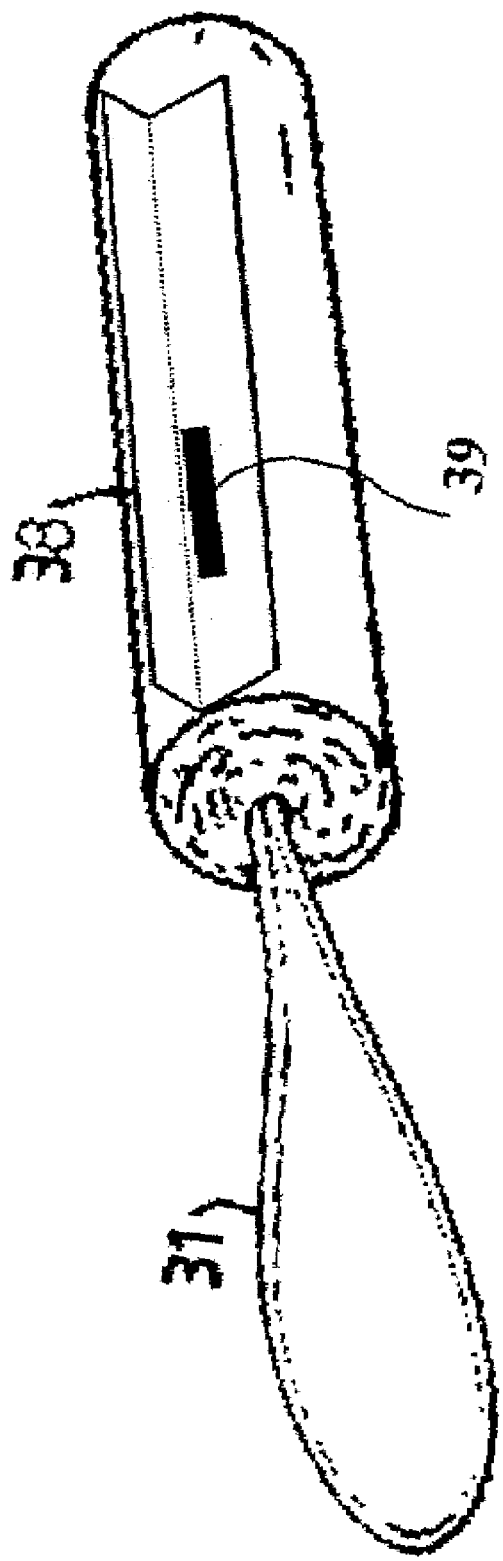
FIG. 8 shows a tampon structure cut open to show a sensing device 39 placed in the absorbing structure of the tampon.

FIG. 8 illustrates an exemplifying embodiment of an absorbent article suitable for the absorption of blood, such as a tampon or similar product comprising an absorbent structure according to the invention comprising one sensing device 39. The tampon comprises an absorbent material, which has been rolled to a cylinder-like form 38. In conjunction with rolling the absorbent material into its cylindrical shape, a string 31 is placed in the center of the cylinder 38 in a conventional manner, and the cylinder 38 is compressed to the desired thickness and shape in a conventional manner. Prior to being compressed and shaped, the absorbent material will suitably have a density range of 0.4–0.9 g/cm$^3$ and a weight per unit area of 200–600 g/m$^2$.

In a further embodiment, the absorbent article suitable for the absorption of blood comprises an absorbent structure of an air-laid web of cellulose fibers used as an absorbent material. The fibers are compressed into a dry-formed sheet having a first density of about 0.2–1.0 g/cm$^3$ and wherein the compressed sheets are mechanically softened by a non-cutting method to a second reduced density, which is lower than the original, first density. The sheets may then be then delaminated so as to form a plurality of partially separated thin fiber layers. Such thin fiber layers exhibit density of about 0.2–1.0 g/cm$^3$. The structure in such an embodiment exhibits a density reduction of, after being softened, up to and including 75% and a weight per unit area of between 30–2000 g/m$^2$.

The absorbent article suitable for the absorption of blood, such as a tampon or similar product comprises the absorbent structure according to an embodiment of the invention. As such, different numbers of sensing devises are included, as mentioned above. In FIG. 7, one sensing device is included in the absorbent structure. The sensor in a tampon like structure needs to be placed in the interior of the absorbent structure.

A Sanitary Napkin

One embodiment of the invention is a sanitary napkin. The napkin may comprise, in a conventional manner, an absorbent structure, which is enclosed between a fluid-permeable top sheet, which may comprise perforated plastic film or like material and which lies proximal to the wearer in use, and a fluid-impermeable bottom sheet. A thin fluid-permeable layer, for instance, of non-woven material, may be placed between the absorbent structure and the top sheet. The top sheet and bottom sheet have parts, which protrude beyond the absorbent structure and the sheets are mutually joined at these protruding parts. The bottom sheet is comprised of a suitable plastic material, for instance polyethylene. It will be understood, however, that other known materials may be used for the top and the bottom sheets within the scope of the invention.

The absorbent structure may comprise one single layer, or several layers. The single layer may consist of a dry-formed material according to one embodiment of the invention, which contains from 0–10% superabsorbent material. A suitable density range in the case of the absorbent structure is 0.6–0.9 g/cm$^3$, while a suitable weight per unit area is 200–300 g/m$^2$. When the absorbent structure is comprised of a chemothermomechanically produced pulp (CTMP)-material or some other material having a yellowish or brownish color, a covering layer of chemical pulp white in color may be applied to the top of the absorbent structure.

A Sensoring Absorbent System

Also included in one embodiment of the invention is a sensoring absorbent system, comprising the absorbent structure according to an embodiment of the invention, optionally being part of the absorbent articles such as the ones described above, and a hand held unit, comprising an excitation coil generating a magnetic field to magnetize said magnetoelastic film and optionally a pick-up coil that detects the magnetoacoustic resonant frequency.

In a further embodiment, the sensoring absorbent system is disposable.

Figure 10:
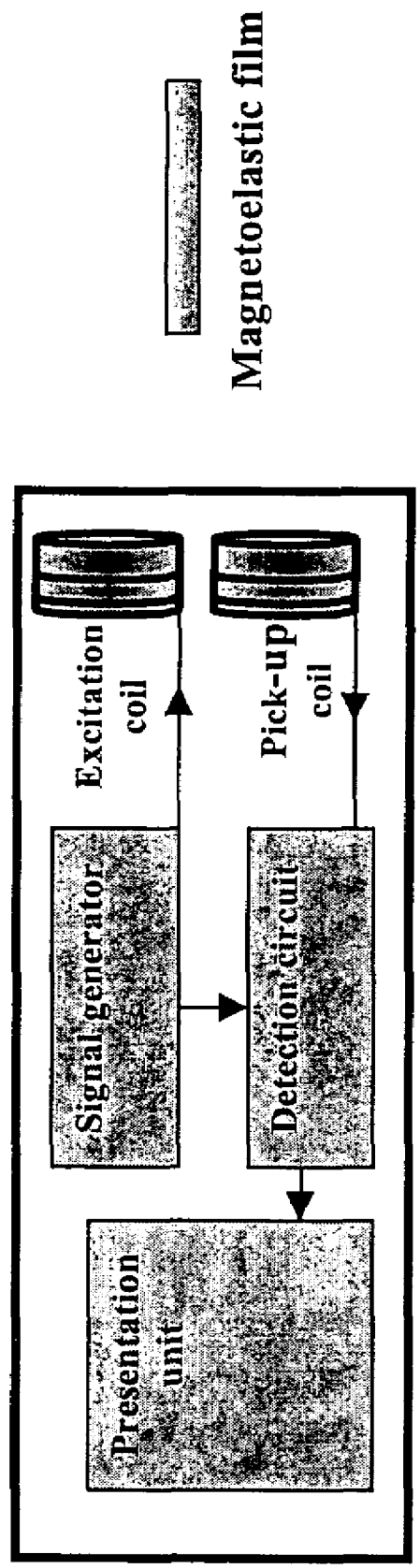
FIG. 10 shows an absorbent sensing unit.

Further embodiments include a signal generator, a detection circuit and a presentation unit, as seen in FIG. 10.

In one embodiment, said sensoring absorbent unit comprises a hand held unit comprising said excitation coil and said pick-up coil.

In the sensoring absorbent unit, the magnetic pulses from the excitation coil must be high enough to sufficiently magnetize the magnetoelastic film so as to enable the pick-up coil to detect the magnetoacoustic signals. This, of course, depends on the distance between the handheld unit and the magnetoelastic film, and to some extent, on the relative orientation between the handheld unit and the magnetoelastic film and may thus be optimized for the specific combination being used.

In one embodiment, METGLAS film is used as the magnetoelastic film. In this embodiment, a magnetic field amplitude of 0.06 mT at the film is high enough in order to detect magnetoacoustic signals. Magnetic pulses of 1 kHz with a duty cycle of 20% was used, but other frequencies and duty cycles may be used. A magnetic field in the range of 0.05 mT to 0.1 mT will create sufficient magnetization in the magnetoelastic film. The exact value depends on the chosen material in the magnetoelastic film, and may thus be optimized for each embodiment. The exact values of the pulse frequency, duty cycle and field amplitude at the film may, in a similar way, be optimized when the material of the magnetoelastic film and the application of the sensor system are chosen. Also, the distance of the hand held unit may be considered here and the value of the maximum distance between the handheld unit and the magnetoelastic film may be defined when optimizing other parameters in the different embodiments. The minimum distance is at the outer surface of the absorbent article. The detection may be designed to enable the largest covering range about x m, where x is chosen by the user of the nursing personnel/care taker by proper design of the excitation coil and the pick-up coil.

In one embodiment, the detection may be designed to enable the largest covering range about x m, where x is about 0–10 m, such as about 0, 1, 2, 3, 4, 5, 6, 7, 8, 9, or 10 m.

In a further embodiment, the detection may be designed to enable the largest covering range about x m, where x is about 0–5 m.

In still a further embodiment, the detection may be designed to enable the largest covering range about x m, where x is about 0–1 m, such as about 0, 0.1, 0.2, 0.3, 0.4, 0.5, 0.6, 0.7, 0.8, 0.9, or 1 m.

Method for Producing an Absorbent Structure

Also included in an embodiment of the present invention is a method for producing an absorbent structure according to an embodiment of the invention, or an absorbent article such as a diaper, a pants-type diaper, incontinence garment, sanitary napkin, wipe, towel, tissue, bed protector, wound or sore dressing, or similar product, comprising the steps of a) providing a liquid-impermeable backing sheet, b) providing at least one wetness sensor and/or at least one biological and/or chemical analyte sensor, c) spraying hot-melt glue onto all or part of the backing sheet, d) attaching at least one absorbent structure onto the backing sheet, e) providing nonwoven on top of the absorbent structure in c), onto the side opposite of the backing sheet, and f) stamping the absorbent product from the nonwoven—absorbent structure—backing sheet structure in e) above.

The sensor in b) above may first be attached to the liquid impermeable backing sheet, and then provided at the same time as the backing sheet.

In another embodiment, the sensor is attached to the backing sheet after the hot-melt glue is sprayed into the backing sheet.

The sensor may also be attached to other parts of the absorbent structure, such as onto, inside, or between different absorbent structures in the absorbent product.

Method for Detecting Wetness, a Bio-analyte, or a Chemical Analyte

Another embodiment of the invention is a method for detecting a chemical analyte, such as wetness, in an absorbent structure according to an embodiment of the invention. The absorbent structure may be incorporated in an absorbent article such as a diaper, a pants-type diaper, incontinence garment, sanitary napkin, wipe, towel, tissue, bed protector, wound or sore dressing, or similar product is contemplated. The method comprises the steps of a) providing an absorbent structure according to an embodiment of the invention, or an absorbent article according to an embodiment of the invention, b) applying a magnetic field, c) exciting the magnetoelastic film in the at least one sensing device in the absorbent structure, d) switching the magnetic field off, e) recording magnetoacoustic resonant frequency, f) optionally repeating step b) to e), and g) detecting changes in the magnetoacoustic resonant frequency, so as to detect wetness and/or at least one biological and/or chemical analyte in the absorbent structure.

The method according to the invention may in further embodiments include a magnetic field, wherein the field is a pulsed magnetic field.

Further embodiments include wherein said magnetoelastic film excited in c) above is excited by an excitation coil.

A further embodiment is wherein the recording in e) above is detected by a pick-up coil.

Even further embodiments include wherein the excitation frequency is swept across the resonance frequency to determine a frequency shift and Q-value changes, where $Q=F/(\Delta F)$, due to absorption of liquid, humidity or moisture, e.g., urine, or desorption of surface coating of the magnetoelastic film, such as the METGLAS film.

FIG. 2 shows a schematic drawing of a sensing device to be used in such as method. FIG. 3 shows a photograph of the same in an experimental set up.

In another embodiment of the method, the excitation coil and optionally the pick-up coil is in a hand held unit, and wherein the hand held unit is 0.1–2 m from the absorbing structure when exciting the magnetoelastic film in c) above and optionally when recording magnetoacoustic resonant frequency in e) above. A hand held unit to be used according to the invention is also disclosed to be used in the method according to the invention. A schematic view is presented in FIG. 4.

In a still further embodiment, a sensing absorbent system described above, may be used in the method.

EXAMPLES

General

In Examples 1–7, the METGLAS film and the capsule used was Ultra-Strip III Narrow from Sensomatic. The capsule also contained a permanent magnet in all of these Examples except Examples 6 and 7.

In Examples 8–11, the METGLAS film used was Ultra-strip III from Sensomatic. In these Examples, prior to the coating step, the METGLAS film was etched in 1 M $NHO_3$, washing with deionized water and acetone and dried. The measurements for these experiments were made in dry state, i.e., dip and dry.

Preparation of the METGLAS Film

In all of the experiments, the capsule was cut open at the short side and the METGLAS film was withdrawn from the capsule. The METGLAS film was then coated in different ways according to different experimental conditions and described in each case below. The coated METGLAS film was then reinserted into the capsule. The upper side of the capsule was split open to allow liquid to penetrate the capsule and reach the coating on the METGLAS film.

The capsule was then wrapped with a surfactant-treated polypropylene nonwoven material. The resulting device (denoted AA) was integrated into the diaper according to the descriptions below.

The Diaper

In all of the experiments, the diaper was composed of 1) liquid-impermeable casing sheet based on polyethylene (ME 1148 from Trioplanex International), 2) cellulose CP fluff pulp (Supersoft Plus from international paper containing 48 g/m$^2$ of superabsorbent polymer (SAP) Drytech S230R from Dow Chemicals), 3) cellulose CTMP fluff pulp (SF 70 HD VSM from Metsä Serla containing 73 g/m$^2$ SAP Drytech S230R from Dow Chemicals), 4) surfactant-treated nonwoven based on polypropylene (Holmestra Spunbond HO18B7W from Fiberweb Sweden), and 5) hot-melt glue (0700108 from National Starch).

Experimental Setup

Figure 11:
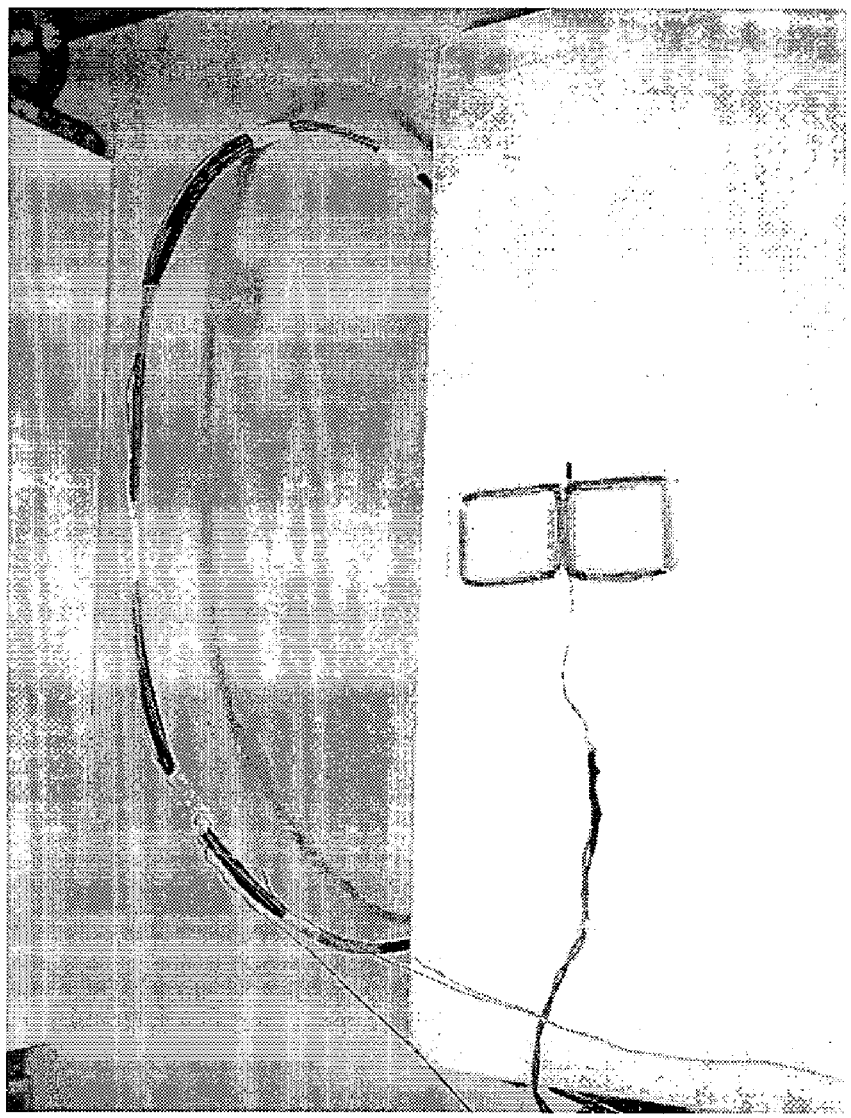
FIG. 11 shows the experimental set-up in the experiments with a circular excitation coil and an eight-shaped pick-up coil.
Figure 12:
FIG. 12 shows a diaper placed in the experimental set-up. The pick-up coil is underneath the diaper (not visible).

In Examples 1–7, the setup included an excitation coil of 25 turns and diameter 25 cm and an eight-shaped detection coil of two 25 turn square coils with a side length of 3 cm. The excitation coil was vertically aligned and the detection coil horizontally aligned along the center axis of the excitation coil as shown in FIG. 11. Referring to FIG. 11, the diaper was placed in such way that the integrated sensor was positioned on top of the detection coil.

A magnetic field is produced on applying an amplitude modulated sinusoidal current to the excitation coil. The amplitude modulation is square-wave shaped, turning the sinusoidal signal on and off with a frequency around 100 Hz and a duty cycle of 10–50 percent. The peak-to-peak value of the applied current is approximately 0.1 A, and the frequency, 10 kHz to 100 kHz. The magnetic field causes a magnetoacoustic oscillation in the METGLAS film. The oscillation induces a voltage in the detection coil. The amplitude and frequency of the voltage in the detection coil is measured with a spectrum analyzer.

In Examples 6 and 7, no permanent magnet was present in the capsule. Thus, the experimental design in these experiments was changed to include an extra circular bias coil of 25 turns and a diameter of 25 cm to produce a magnetic bias field and the bias coil was given a current of 2.2 A, thus generating a magnetic field of approximately 200 mT. This bias-field replaces the bias magnet, i.e., the permanent magnet, used in the other experiments. The bias coil is placed in the same position as the excitation coil.

Figure 24:
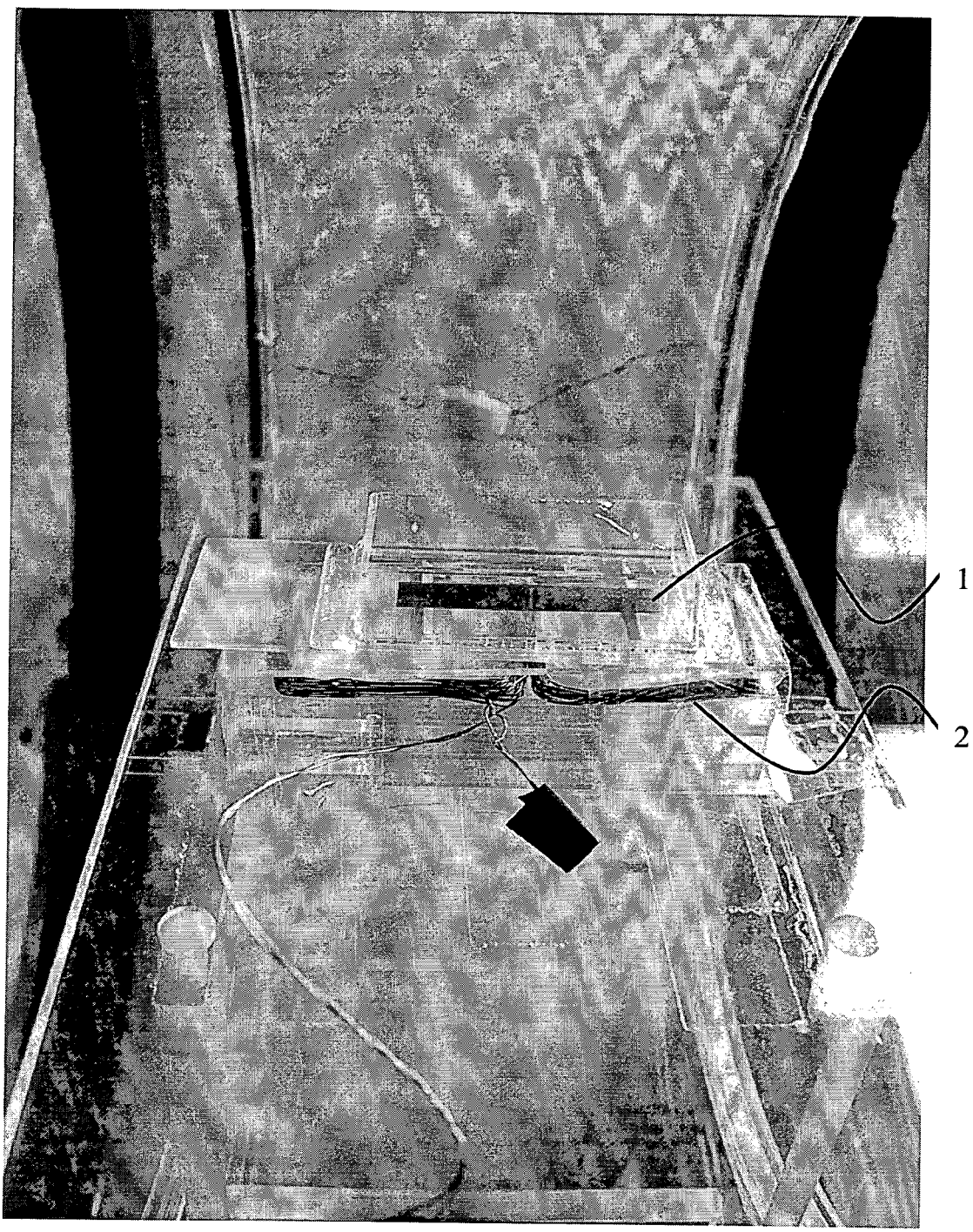
FIG. 24 shows a close-up on the center of the experimental setup, showing a device under test 1 and the figure eight-shaped excitation/detection coil 2.

In Examples 8–11, the device being tested was placed 8 mm above a figure eight-shaped coil, as shown in FIG. 24. The figures eight-shaped coil was constructed by connecting two 25 turn square coils with side length of 3 cm. The figure eight-shaped coil was used both for excitation and for detection. The figure eight-shaped coil was connected to a magnetoelastic resonance detection system, containing a signal generator, a detection circuit, and a data acquisition unit. The acquired data was exported to a desktop computer where the data was analyzed. The setup also included a Helmholtz coil of 100 turns (each coil) with a diameter of 19.5 cm. The Helmholtz coil was used to produce a homogenous magnetic bias field around the device being tested.

Figure 25:
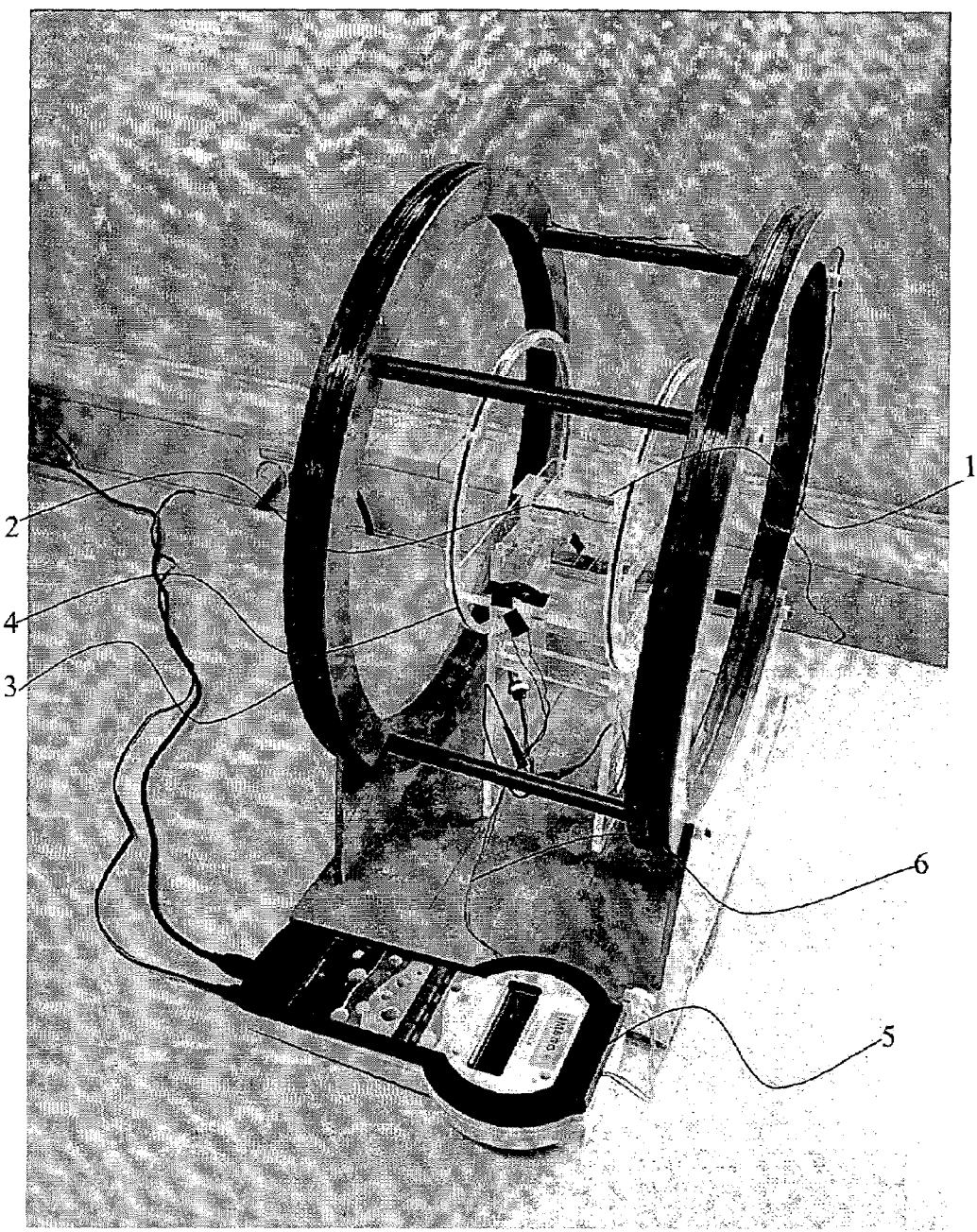
FIG. 25 shows an overview of the experimental setup in experiment 7–11. The device of test 1 is placed horizontally in the center of the setup. Below sample 1 is a figure eight-shaped pickup/detection and excitation coil 2. The outermost coil pair is a Helmholtz coil 3 used for applying a homogenous magnetic field. The concentric coil 4 pair within the Helmholtz coil 3 was not used in these measurements. A magnetoelastic detection unit 5 is seen below the coils. The magnetoelastic detection unit 6 is connected to the excitation detection coil 2.

A current of 0.9 A was passed through the Helmholtz coil producing a magnetic field of approximately 0.4 mT. To excite the device, a magnetic field was generated by passing a sinusoidal current through the figure eight-shaped coil. The amplitude of the current was approximately 30 mA and the frequency 50 kHz to 60 kHz. The excitation signal was switched off after 5 ms. The oscillation of the device induced a voltage in the figure eight-shaped coil which was detected. The amplitude and the frequency of the induced voltage were analyzed using MATLAB software (The MathWorks, Inc.) on a desktop computer. An overview of the experimental setup is seen in FIG. 25.

Example 1

Wet Sensor Coated with a Hydrophilic Linear Polymer

Objective

The objective of this example is to analyze wetness in a diaper using a wet sensor coated with a hydrophilic linear polymer.

Materials and Methods

The METGLAS film was coated with a 1% (w/w) polyvinylpyrrolidone (PVP) solution.

PVP with a molecular weight of 360 kDa was supplied from Scientific Polymer Products. The METGLAS film was dried at 70(C and a PVP-coating was formed on the METGLAS film. The PVP film was thin and weighed in total 0.017 g.

The sensor was included in the absorbent structure by attaching the AA-device to the liquid impermeable backing sheet 27 cm from the center front of the liquid impermeable casing sheet.

The absorbent structure was covered with two cellulose fluff pulp materials in the following order: CP followed by CTMP.

Finally, the surfactant-treated nonwoven was placed at the top.

Results

A total amount of 100 ml synthetic urine was added in three aliquots at different time points: 20 ml at 60 s, 20 ml at 560 s and 60 ml at 1050 s.

The wetting point was located 36 cm below the center front of the impermeable backing sheet.

Figure 13:
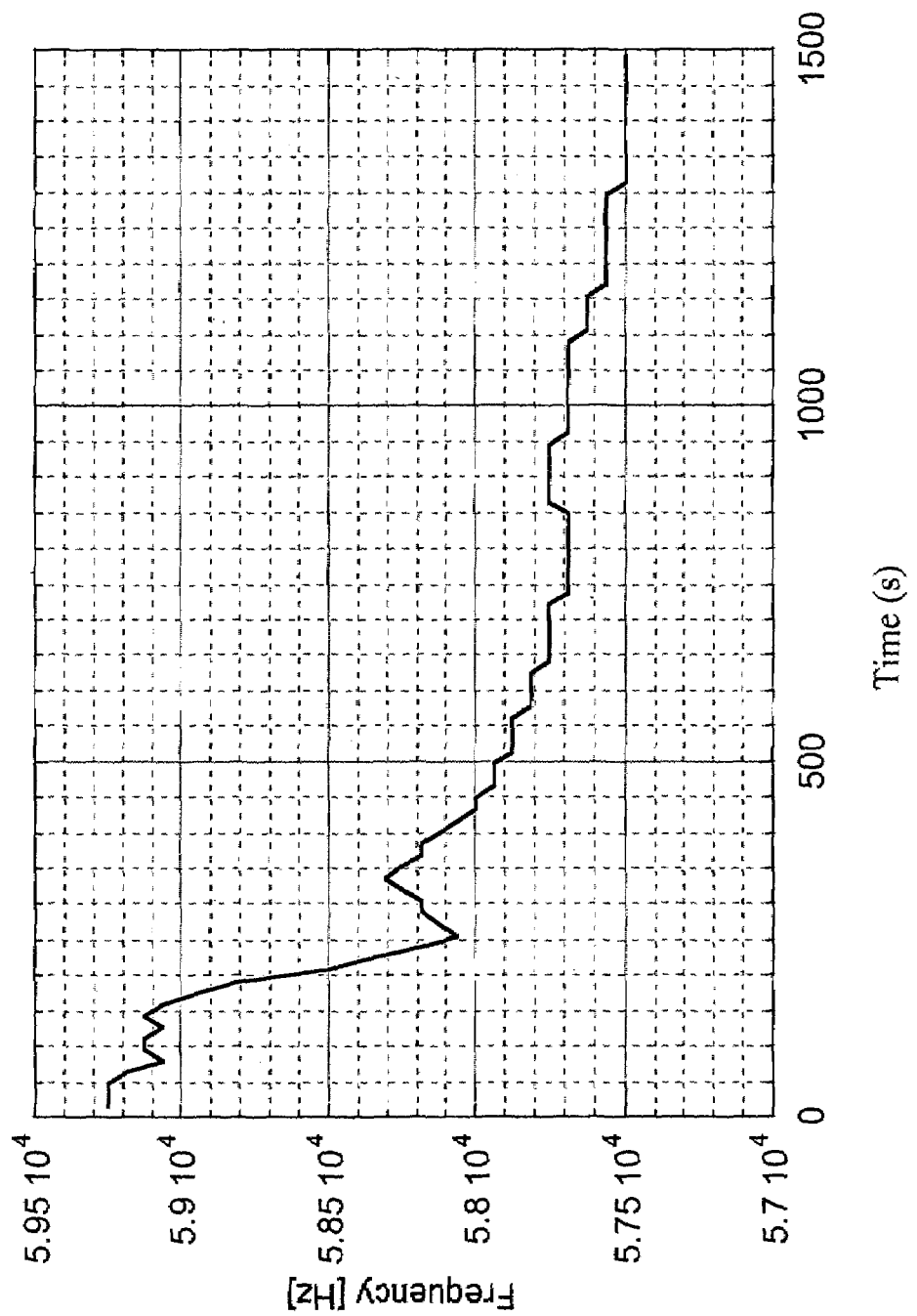
FIG. 13 shows a frequency shift from $5.93 \times 10^4$ Hz to $5.75 \times 10^4$ Hz when the synthetic urine is detected by the wetness sensor coated with polyvinylpyrrolidone (PVP).
Figure 14:
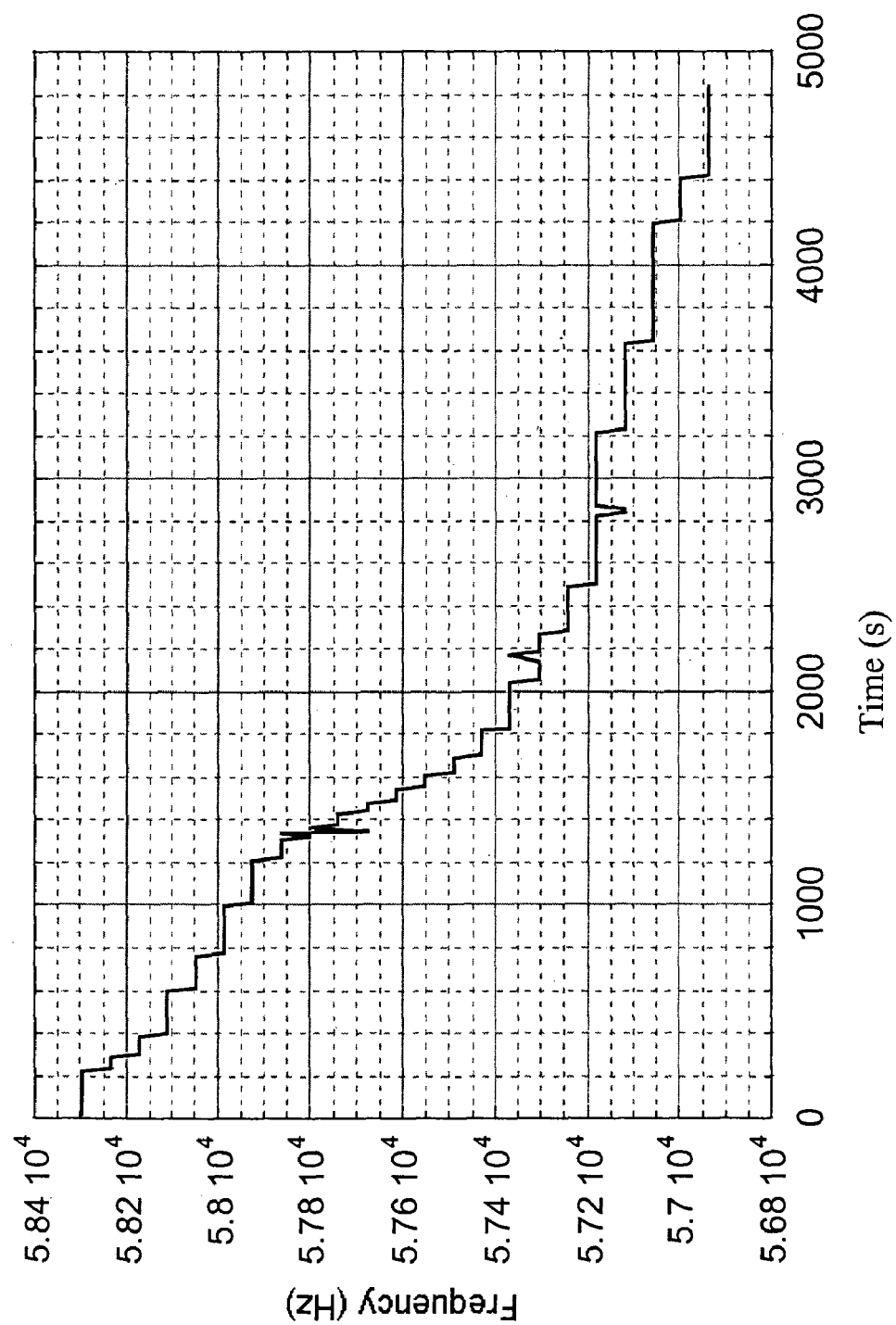
FIG. 14 shows a frequency shift from $5.83 \times 10^4$ Hz to $5.69 \times 10^4$ Hz when the synthetic urine is detected by the wetness sensor coated with cross-linked polyvinylalcohol (PVOH).
Figure 15:
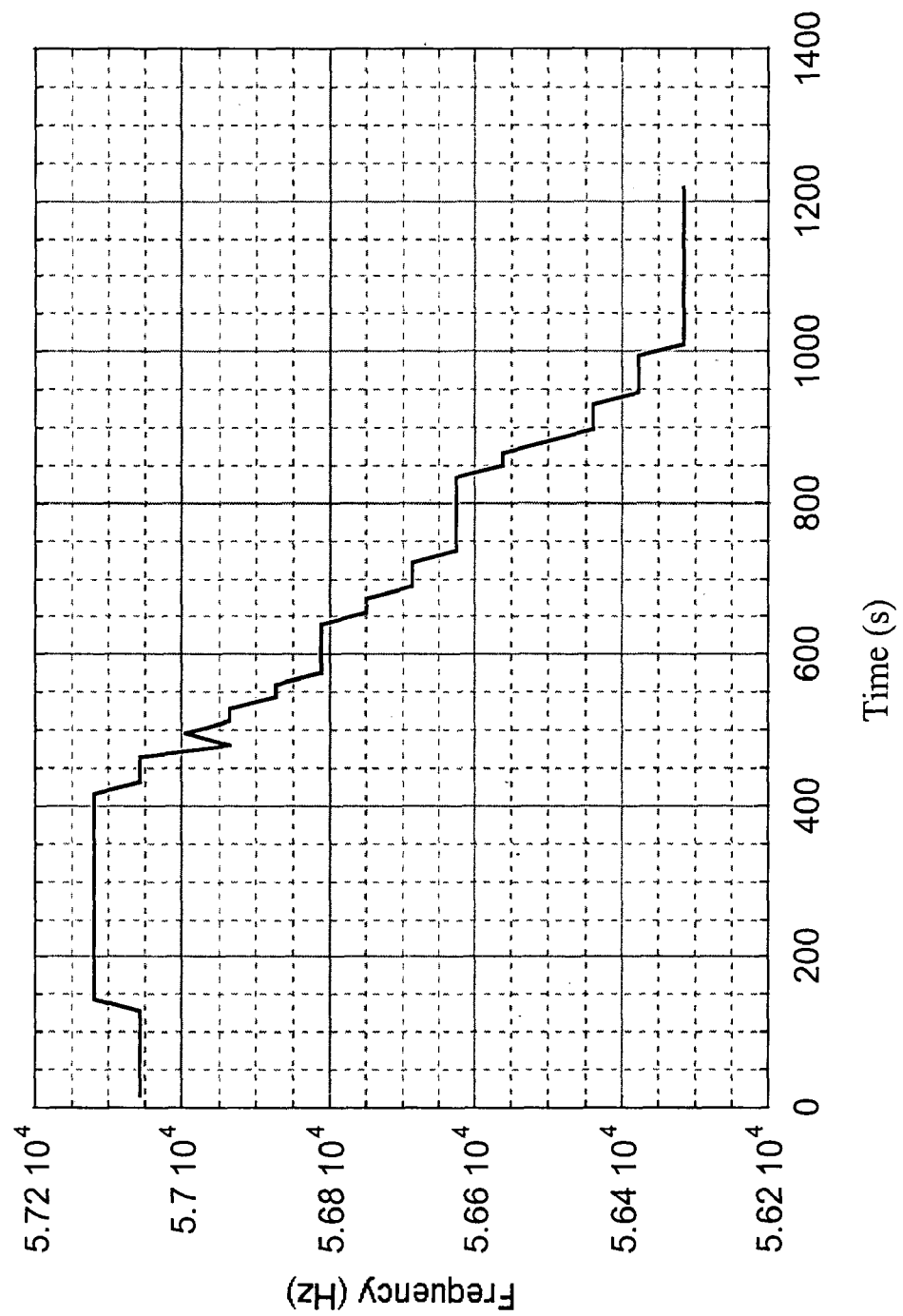
FIG. 15 shows a frequency shift from $5.71 \times 10^4$ Hz to $5.63 \times 10^4$ Hz when the synthetic urine is detected by the wetness sensor coated with sodium chloride (NaCl).
Figure 16:
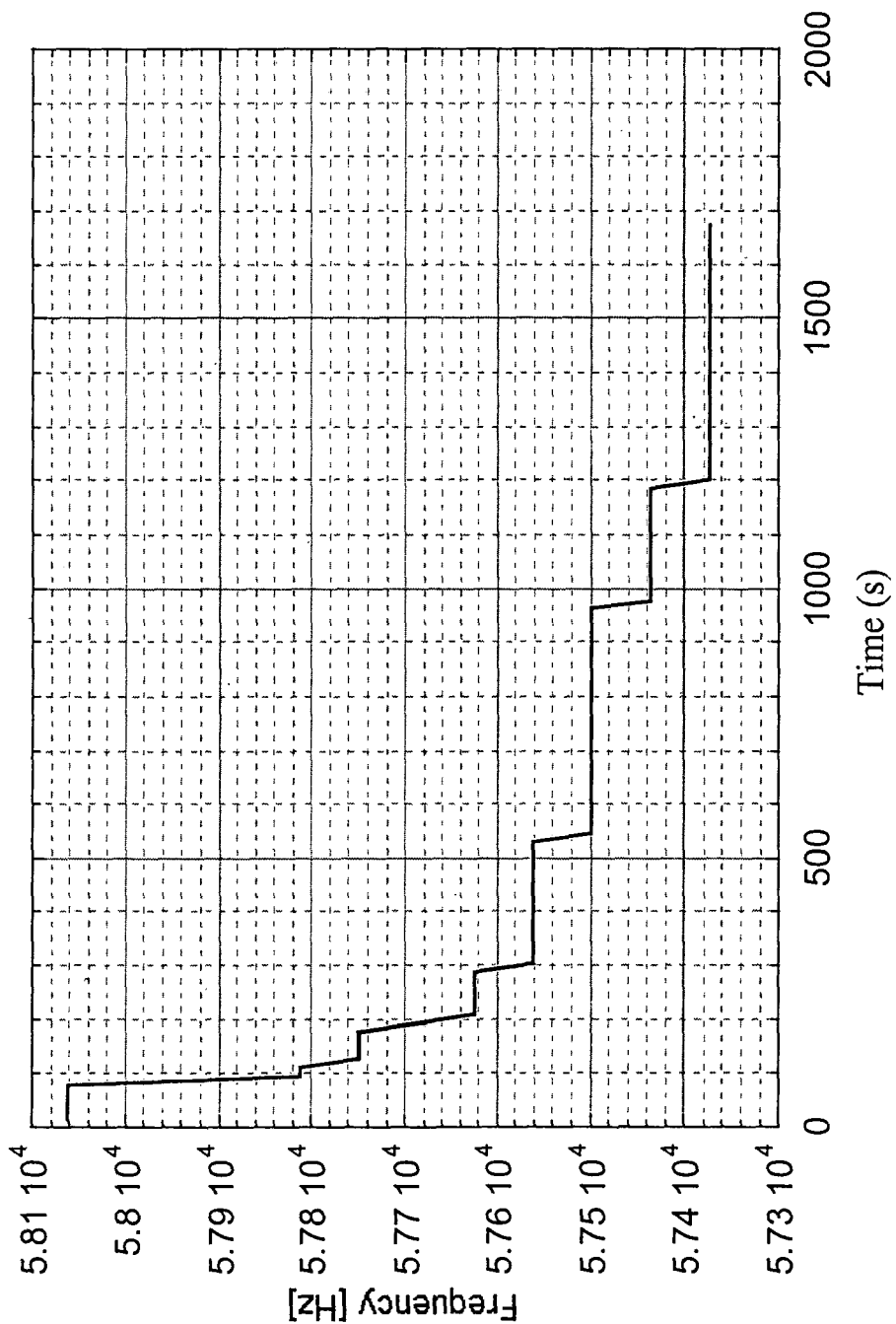
FIG. 16 shows a frequency shift from $5.81 \times 10^4$ Hz to $5.74 \times 10^4$ Hz when the AA-device is attached to the absorbent structure 27 cm from the center front of the liquid impermeable backing sheet
Figure 17:
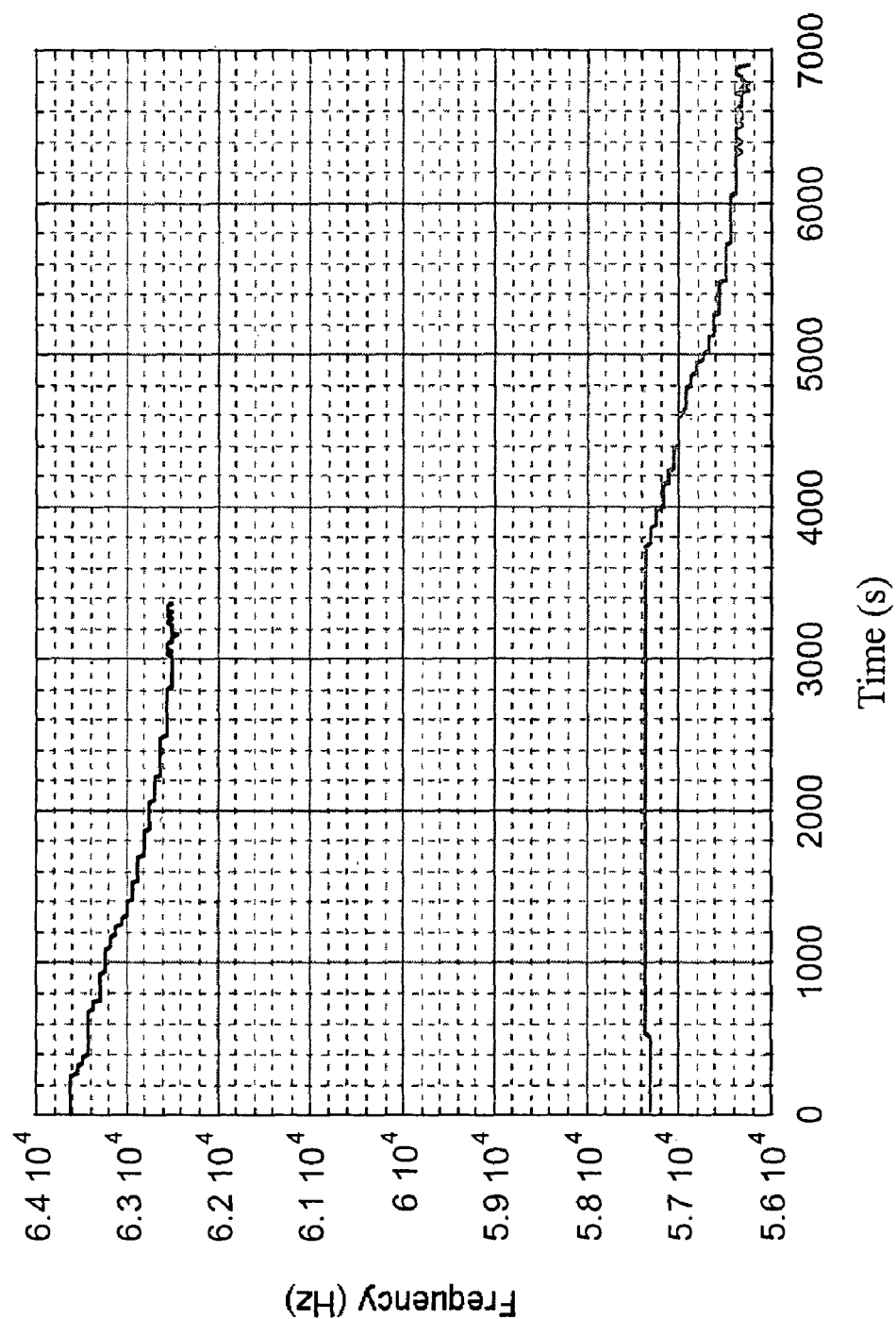
FIG. 17 shows a frequency shift from two different sensors placed at different positions in the absorbent structure.
Figure 18:
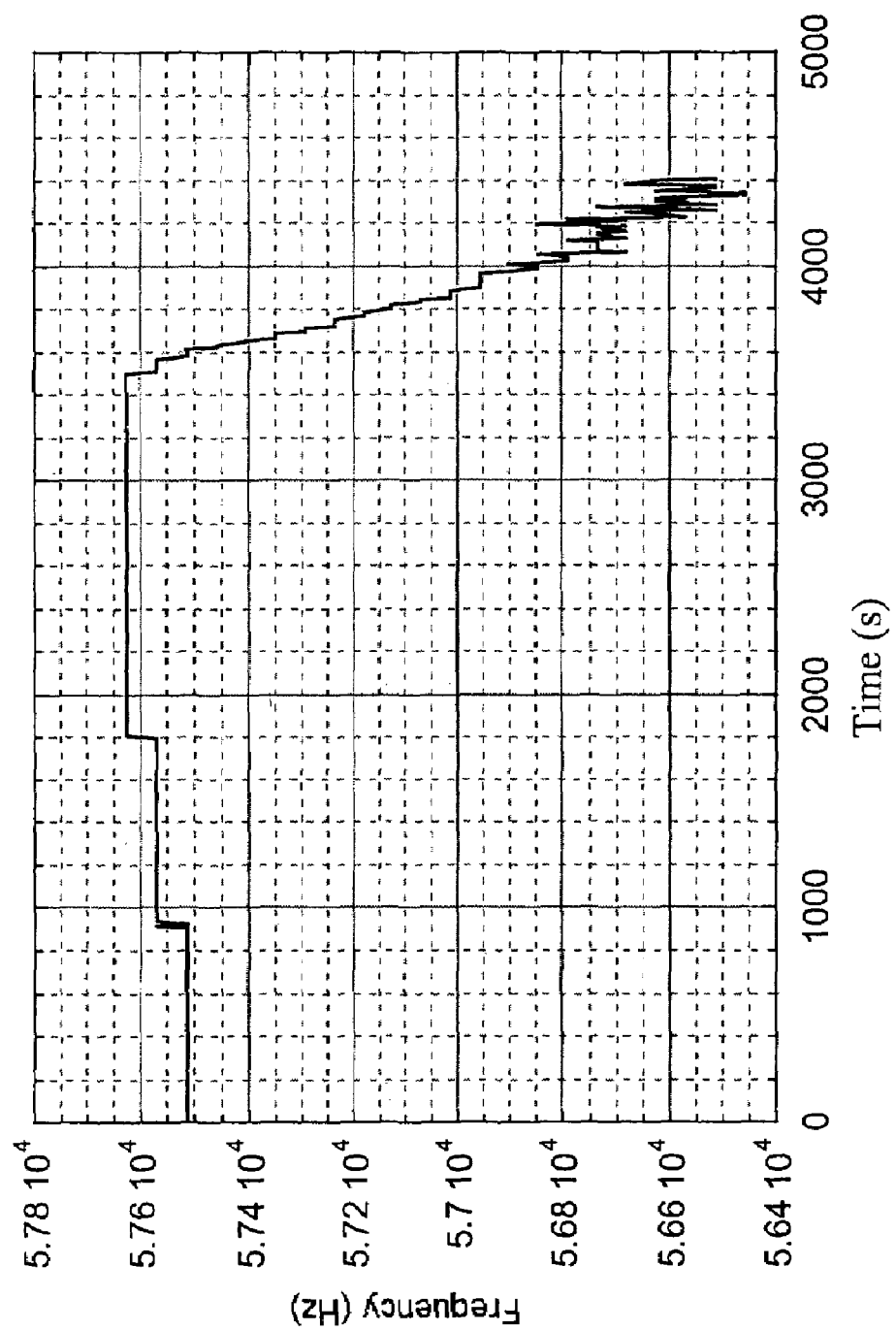
FIG. 18 shows a frequency shift from $5.76 \times 10^4$ Hz to $5.66 \times 10^4$ Hz when using a sensor without encapsulation of the METGLAS film.
Figure 19:
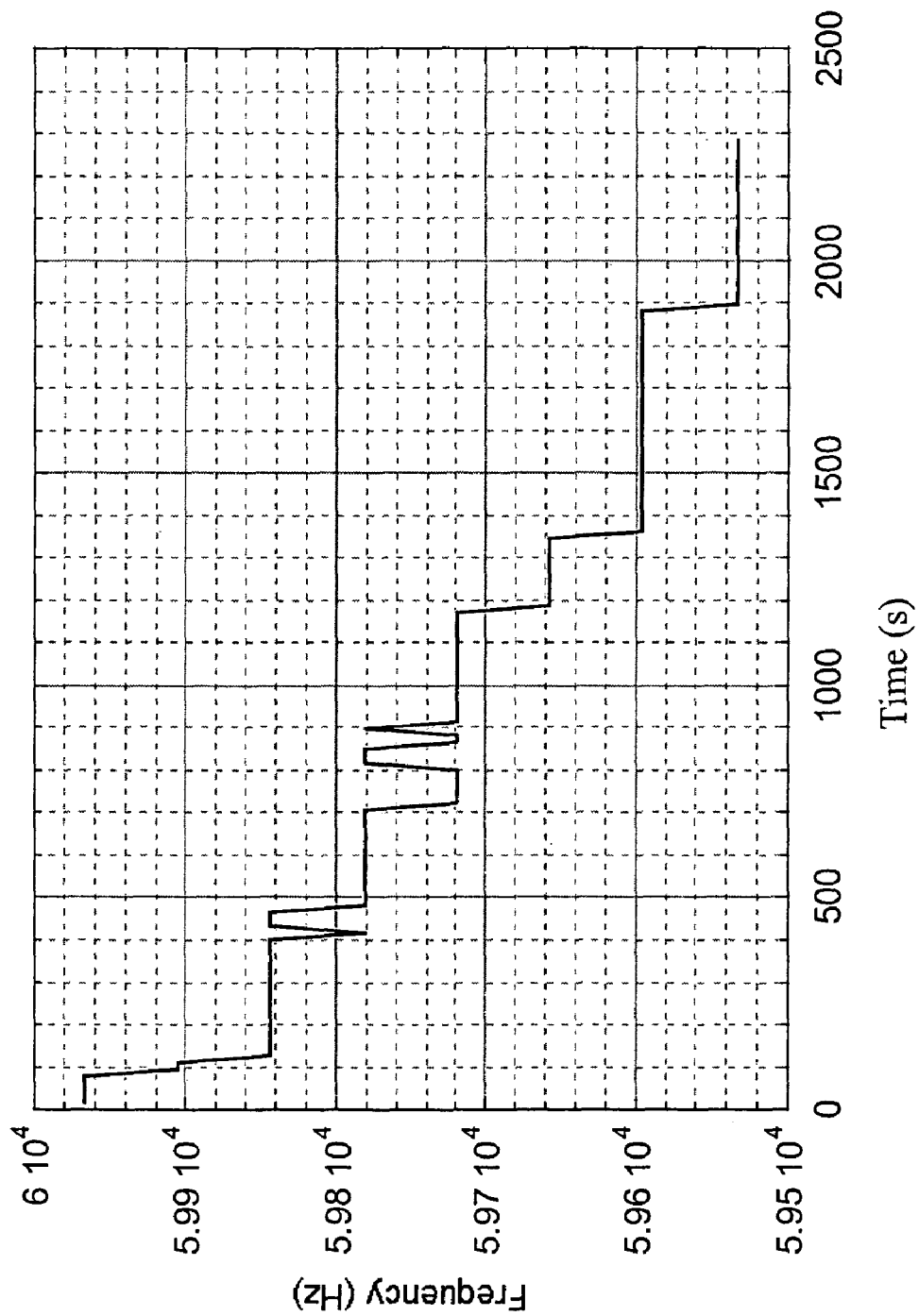
FIG. 19 shows a frequency shift from $6.00 \times 10^4$ Hz to $5.95 \times 10^4$ Hz when using a sensor without a permanent magnet.

The frequency shifted from $5.93 \times 10^4$ Hz to $5.75 \times 10^4$ Hz as shown in FIG. 13.

Conclusions

The change in frequency shows that the sensor absorbs the synthetic urine. The sensor thereby changes its resonance frequency due to a density shift of the coated METGLAS film when absorbing the synthetic urine.

Example 2

Wet Sensor Coated with a Hydrophilic Crosslinked Polymer

Objective

The objective of this example is to analyze wetness in a diaper using a wet sensor coated with a hydrophilic crosslinked polymer.

Materials and Methods

The METGLAS film was coated with a gel based on slightly crosslinked polyvinyl alcohol (PVOH). The gel was formed by mixing 1 part of 5% (w/w) PVOH-solution with 1.5 parts of 4% (w/w) di-sodium tetraborate decahydrate. The gel is formed after 5 minutes of mixing. The gel is then rolled onto the METGLAS film and dried in room-climate for at least 12 hours. The dried film weighed in total 0.0011 g.

PVOH had a molecular weight of 125 kDa (supplied from Scientific Polymer Products) and di-sodium tetraborate decahydrate (pro analysi) was supplied from Merck.

The product was made by attaching the AA-device to the liquid-impermeable backing sheet 27 cm from center front of the liquid-impermeable casing sheet. The absorbent structure was covered with two cellulose fluff pulp materials in the following order: CP and CTMP. Finally, the surfactant-treated nonwoven was placed at the top.

Results

A total amount of 250 ml synthetic urine was added in five aliquots: 20 ml at 120 s, 20 ml at 600 s, 60 ml at 1200 s, 50 ml 3050 s and 100 ml 4000 s.

The wetting point was located 36 cm below the center front of the impermeable backing sheet. The frequency shifted from $5.83 \times 10^4$ Hz to $5.69 \times 10^4$ Hz.

Conclusions

The change in frequency shows that the sensor absorbs the synthetic urine. The sensor thereby changes its resonance frequency due to a density shift of the coated METGLAS film when absorbing the synthetic urine.

Example 3

Wet Sensor Coated with a Low Molecular Weight Compound

Objective

The objective of this example is to analyze wetness in a diaper using a wet sensor coated with a low molecular weight compound.

Materials and Methods

The METGLAS film was coated with 12% (w/w) sodium chloride (NaCl) solution.

NaCl (pro analysi) was supplied by Aldrich. The METGLAS film was dried at 70(C and NaCl crystals were formed on the METGLAS film. The NaCl crystals weighed 0.003 g.

The product was made by attaching the AA-device to the liquid-impermeable backing sheet 27 cm from center front of the liquid-impermeable casing sheet.

The absorbent structure was covered with two cellulose fluff pulp materials in the following order: CP and CTMP. Finally the surfactant-treated nonwoven was placed at the top.

Results

A total amount of 100 ml synthetic urine was added in three aliquots: 20 ml at 80 s, 20 ml at 305 s and finally 60 ml at 840 s.

The wetting point was located 36 cm below the center front of the impermeable backing sheet. The frequency shifted from $5.71 \times 10^4$ Hz to $5.63 \times 10^4$ Hz.

Conclusions

The change in frequency shows that the sensor absorbs the synthetic urine. The sensor thereby changes its resonance frequency due to a density shift of the coated METGLAS film when the salt is hydrolyzed on the METGLAS film thereby absorbing the synthetic urine.

Example 4

Sensors at Different Cross-section Positions in the Absorbent Structure

Objective

The objective of this example is to analyze wetness in a diaper using a wet sensor coated positioned at different cross-sections in an absorbent structure. The position of the sensor in this experiment should be compared to the sensor position in Example 1.

Materials and Methods

The METGLAS film was coated with 1% (w/w) polyvinylpyrrolidone (PVP) solution.

PVP was supplied from Scientific Polymer Products and had a molecular weight of 360 kDa. The METGLAS film was dried at 70(C and a PVP-coating was formed on the METGLAS film. The PVP film was thin and weighed in total 0.017 g.

The product was made by placing the CP fluff pulp on the liquid-impermeable backing sheet. The AA-device was attached to this absorbent structure 27 cm from center front of the liquid impermeable backing sheet. Compare the position with the position in Example 1.

The CTMP absorbent structure was placed above. Finally, the surfactant-treated nonwoven was placed at the top.

Results

A total amount of 100 ml synthetic urine was added in three aliquots: 20 ml at 80 s, 20 ml at 675 s and 60 ml at 1075 s.

The wetting point was located 36 cm below the center front of the impermeable backing sheet. The frequency shifted from $5.81 \times 10^4$ Hz to $5.74 \times 10^4$ Hz.

Conclusions

The change in frequency in this example should be compared to the frequency change in Example 1. The two different positions give different changes in the frequency.

Also, due to the different positions, the change in frequency starts at different time points, i.e., after 150 s in Example 1 and after about 85 s in Example 4.

Thus, different positions of the wet sensor in an absorbent structure may be used to monitor the spread of liquid, such as urine, or humidity in the product.

Example 5

Two Sensors Placed at Different Positions in an Absorbent Structure

Objective

The objective of this example is to analyze a frequency shift when using two sensors placed at different positions in an absorbent structure.

Materials and Methods

Two METGLAS films were coated with 1% (w/w) polyvinylpyrrolidone (PVP) solution.

PVP had a molecular weight of 360 kDa (supplied from Scientific Polymer Products).

The METGLAS film was dried at 70(C and a PVP-coating was formed on the METGLAS film. The PVP film was thin and weighed in total 0.017 g. One of the METGLAS films was cut 3 mm shorter than the other.

The product was made by attaching the AA-devices to the liquid impermeable backing sheet 27 cm and 60 cm respectively from the center front.

The absorbent structure was covered with two cellulose fluff pulp materials in the following order: CP and CTMP. Finally, the surfactant-treated nonwoven was placed at the top.

Results

A total amount of 460 ml synthetic urine was added in seven aliquots: 20 ml at 140 s, 20 ml at 640 s, 60 ml at 1100 s, 60 ml at 2050 s, 100 ml at 2700 s, 100 ml at 3300 s and finally 100 ml at 4600 s.

The wetting point was located 36 cm below the center front of the impermeable backing sheet. The frequency shifted first for the sensor placed 27 cm from center with a change from $6.36 \times 10^4$ Hz to $6.26 \times 10^4$ Hz and thereafter for the sensor placed 60 cm from the center front with a change from $5.74 \times 10^4$ Hz to $5.64 \times 10^4$ Hz.

Conclusions

This experiment shows a simple and clean way of detecting a frequency shift indicated by two sensors placed in one absorbent structure at two different positions. The different positions of the two sensors led to a kinetic difference of the frequency change. Such a difference may be used to calculate quantitative changes of the amount of liquid spread in the absorbent structure, when the wetting profile of a specific absorbent structure is known.

Example 6

Sensors Without Encapsulation of the METGLAS Film

Objective

The objective of this example is to analyze a frequency shift when using a sensor without encapsulation of the METGLAS film.

Materials and Methods

The METGLAS film was coated with a gel based on partially crosslinked polyvinylalcohol PVOH. The gel was formed by mixing 1 part of 5% (w/w) PVOH-solution with 1.5 parts of 4% (w/w) di-sodium tetraborate decahydrate. The gel was formed after 5 min of mixing. The gel was rolled onto the METGLAS film and dried in room temperature for at least 12 hours. The dried film weighed in total 0.0039 g.

PVOH was purchased from Scientific Polymer Products and had a molecular weight of 125 kDa and di-sodium tetraborate decahydrate (pro analysi) was supplied from Merck.

The product was made by placing the CP fluff pulp the liquid impermeable backing sheet. The coated METGLAS film was placed without a capsule onto the absorbent structure 41 cm from the center front of the liquid impermeable backing sheet.

The CTMP absorbent structure was placed above. Finally, surfactant-treated nonwoven was placed at the top.

Results

A total amount of 170 ml synthetic urine was added in five aliquots: 20 ml at 190 s, 20 ml at 570 s, 20 ml at 1300 s, 40 ml at 1980 s and finally 50 ml at 3350 s.

The wetting point was located 36 cm below the center front of the impermeable backing sheet. The frequency shifted from $5.76 \times 10^4$ Hz to $5.66 \times 10^4$ Hz.

Conclusions

The change in frequency shows that the wet sensor also works without encapsulation.

Example 7

Sensors Without a Permanent Magnet

Objective

The objective of this example is to analyze a frequency shift when using a sensor without a permanent magnet.

The frequency shifted from $6.00 \times 10^4$ Hz to $5.95 \times 10^4$ Hz.

Material and Methods

The METGLAS film was coated with 1% (w/w) polyvinylpyrrolidone (PVP) solution.

PVP was supplied from Scientific Polymer Products and had a molecular weight of 360 kDa. The METGLAS film was dried at 70° C. and a PVP-coating was formed on the METGLAS film. The PVP film was thin and weighed in total 0.017 g.

The device AA was changed compared to the general description for the other experiments. The permanent magnet was dismantled from the capsule thereby forming the device named "AA."

The product was made by attaching the AA device to the liquid-impermeable backing sheet 27 cm from center front of liquid-impermeable casing sheet.

The absorbent structure was covered with two cellulose fluff pulp materials in the following order: CP and CTMP. Finally the surfactant-treated nonwoven was placed at the top.

Results

A total amount of 200 ml synthetic urine was added in four aliquots: 20 ml at 70 s, 20 ml at 450 s, 60 ml at 1100 s and finally 100 ml at 2000 s The wetting point was located 36 cm below the center front of the impermeable backing sheet. The frequency shifted from $6.00 \times 10^4$ Hz to $5.95 \times 10^4$ Hz.

Example 8

Biosensor for Detection of *Staphylococcus Aureus* Using METGLAS Coated with a Cationic Polymer Objective The objective of this example is to detect the pathogen *S. aureus* in a target solution using a biosensor based on Metglas coated with a cationic polymer and primary antibodies.

Materials and Methods

Polyethyleneimine, PEI, a high molecular weight water free polymer and glutaraldehyde sol 50% in water were purchased from Sigma-Aldrich. Mouse monoclonal antibody to *S. aureus* peptidoglycan was purchased from Abcam Limited. CCUG 10778 *S. aureus* was purchased from University of Gothenburg, Department of Clinical Bacteriology.

The METGLAS film was coated with PEI by dip coating in a 0.5% (w/w) PEI/methanol solution. The METGLAS was removed from the coating solution and air-dried to allow solvent evaporation. Chemical cross-linking was carried out by exposing the thin polymer layer to the vapors of a 5% (v/v) glutaraldehyde/phosphate buffer saline solution (pH 7.0) for 2 h at room temperature. The METGLAS was removed from the glutaraldehyde environment and placed in a heating oven at 100° C. for 4 minutes.

Finally, the monoclonal antibody (mAb) was immobilized onto the coated surface of the sensor. 200 µl mAb solution (1.4 mg/ml) was added on the polymer layer and incubated at room temperature for 1 h. After the incubation step, the mAb solution was removed; the surface was washed with PBS pH 7.2 and air-dried.

*S. aureus* was growth in TSB medium at 37° C. overnight. The bacterial suspension was centrifuged, the supernatant was discarded and the bacterium resuspended in 0.9% NaCl.

Measurement Procedure

The frequency for the dry biosensor was first determined, and then the biosensor was immersed in 3 ml bacterial suspension for 58 minutes at room temperature. The sensor was removed from the suspension, air-dried and the new frequency was measured.

Results

Figure 20:
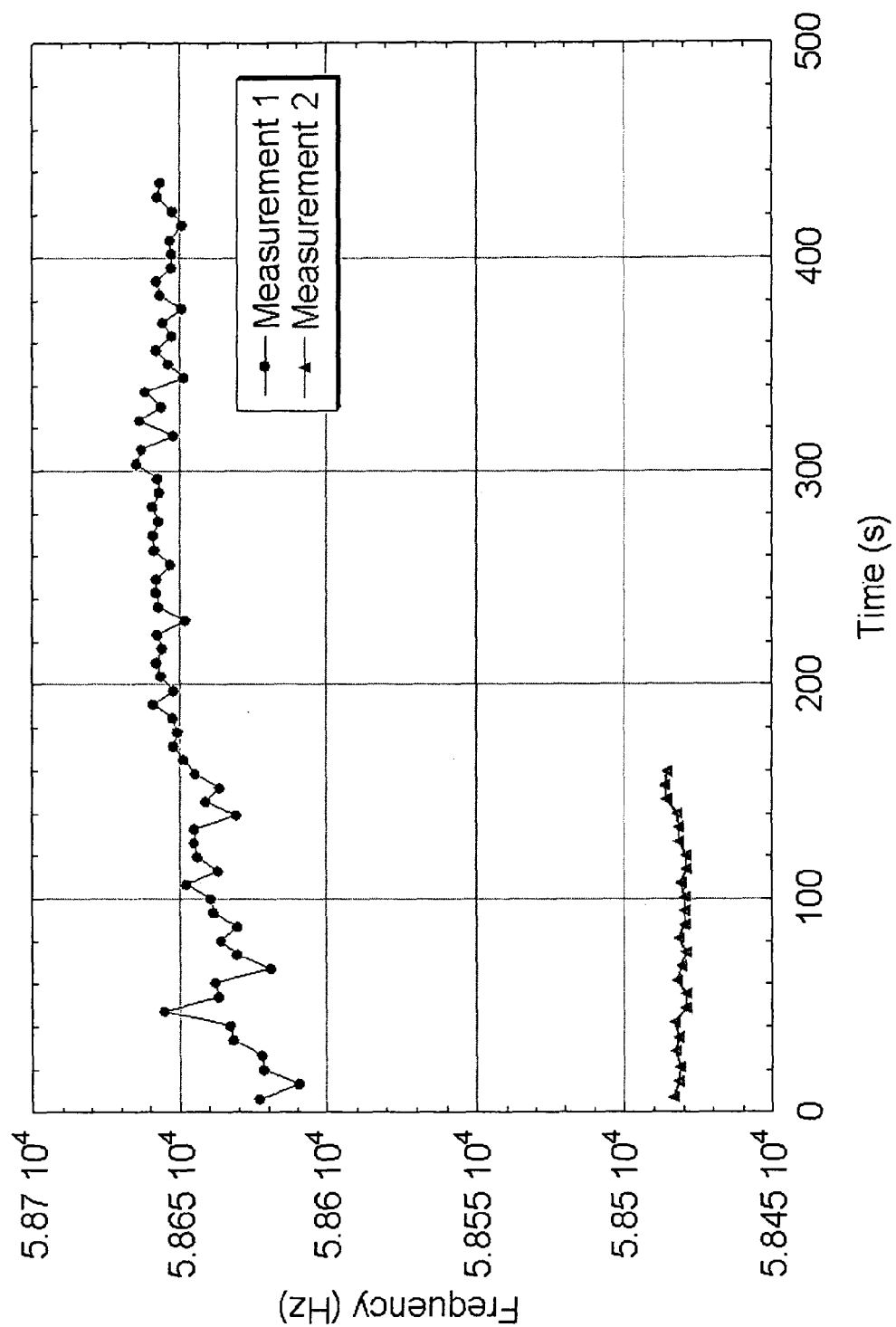
FIG. 20 shows a frequency shift from 58680 Hz to 58480 Hz when using METGLAS coated with a cationic polymer.

As seen in FIG. 20, measurement 1 gave the frequency (f) 58680 Hz and measurement 2 gave f 58480 Hz.

The Δf is 200 Hz.

Conclusions

The frequency shift indicates binding of the target species to the biosensor. The change in frequency shows the response of the sensor to additional surface mass load.

Example 9

Biosensor for Detection of *Staphylococcus Aureus* Using METGLAS Coated with a Colloidal Suspension Objective The objective of this example is to detect the pathogen *S. aureus* in a target solution using a biosensor based on METGLAS coated with a polystyrene bead and primary antibodies.

Materials and Methods

Polybead Polystyrene (PS) microspheres (2.65% solids-latex, θ 1µ) was purchased from Scientific Polymer Products. Mouse monoclonal antibody to *S. aureus* peptidoglycan was purchased from Abcam Limited. CCUG 10778 *S. aureus* was purchased from University of Gothenburg, Department of Clinical Bacteriology.

The METGLAS film was coated with PS microspheres by dip coating in a 2.5% Ps-latex colloidal suspension. The METGLAS was immersed in 2 ml coating solution for 30 minutes at room temperature. The METGLAS was removed from the coating suspension and placed in a heating oven at 50° C. for 15 minutes. Finally, the monoclonal Ab was immobilized onto the coated surface of the sensor.

The coated METGLAS was immersed in 400 µl Ab solution (1.4 mg/ml) and incubated at room temperature for 1 h. After the incubation step, the Ab solution was removed and the sensor was air dried at room temperature.

*S. aureus* was growth in TSB medium at 37° C. overnight. The bacterial suspension was centrifuged, the supernatant was discarded and the bacterium resuspended in 0.9% NaCl.

Measurement Procedure

First, the frequency for the dry biosensor was determined, and then the biosensor was immersed in 3 ml bacterial suspension for 45 minutes at room temperature. The sensor was removed from the suspension, air-dried, and the new frequency was measured.

Results

Figure 21:
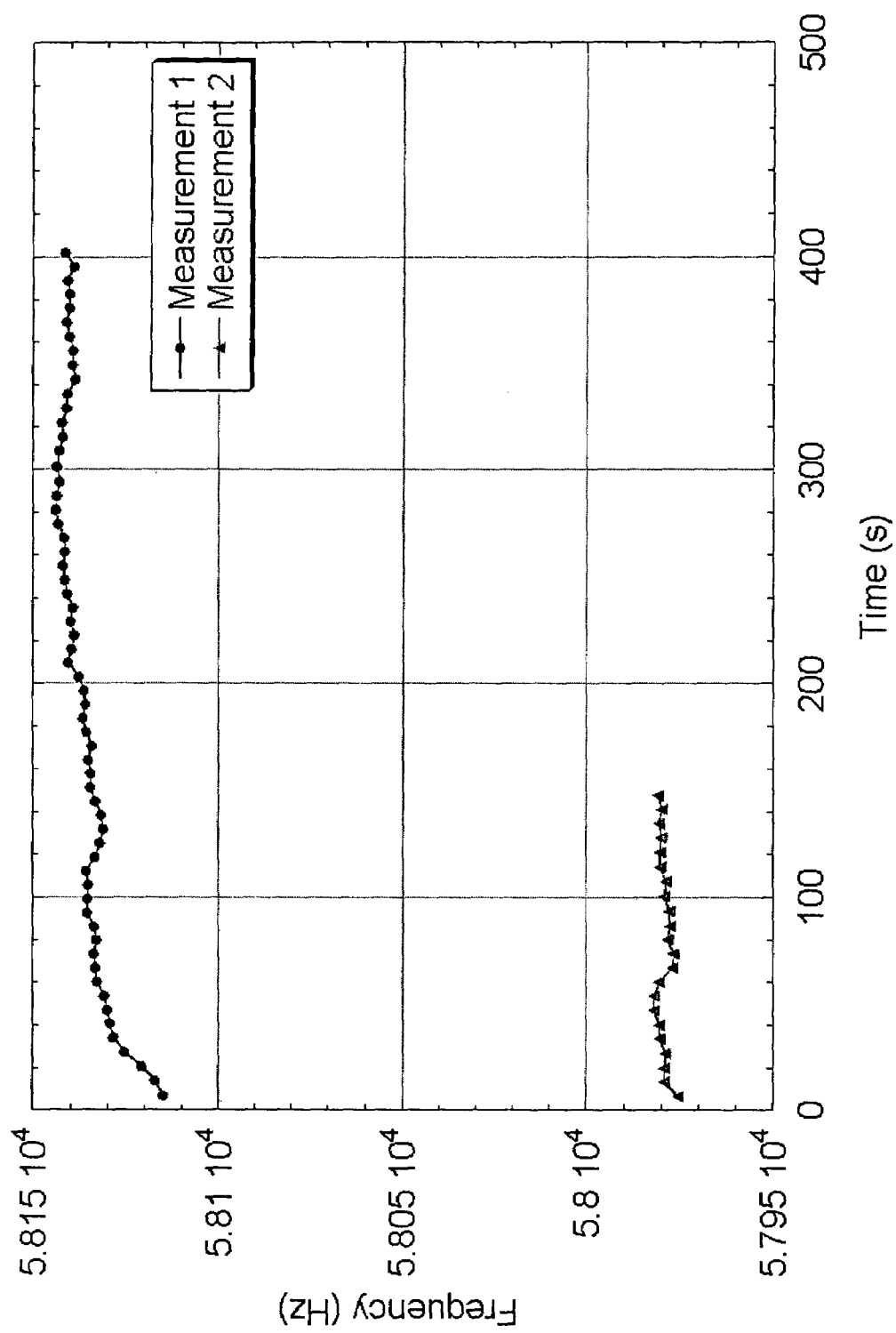
FIG. 21 shows a frequency shift from 58140 Hz to 57980 Hz when using METGLAS coated with a colloidal suspension.

As seen in FIG. 21, measurement 1 gave f 58140 Hz and measurement 2 gave f 57980 Hz.

The Δf is 160 Hz.

Conclusions

The change in frequency shows the response of the sensor to additional surface mass load. The frequency shift indicates binding of the target species to the biosensor.

Example 10

Biosensor for Detection of *Staphylococcus Aureus* Using METGLAS Coated with a Hydrophobic Polymer Objective The objective of this example is to detect the pathogen *S. aureus* in a target solution using a biosensor based on METGLAS coated with a hydrophobic polymer and primary antibodies.

Materials and Methods

Polystyrene with a molecular weight of 45 kDa was purchased from Scientific Polymer Products. Mouse monoclonal antibody to *S. aureus* peptidoglycan was purchased from Abcam Limited. CCUG 10778 *S. aureus* was purchased from University of Gothenburg, Department of Clinical Bacteriology.

The METGLAS film was coated with polystyrene (PS) by dip coating in a 1% (w/w) PS/toluene solution. The METGLAS was removed from the coating solution and air-dried to allow solvent evaporation. The METGLAS was placed in a heating oven at 100° C. for 4 minutes.

Finally, the monoclonal Ab was immobilized onto the coated surface of the sensor. 200 μl stock solution of mAb (1.4 mg/ml) was added on the polymer layer and incubated at room temperature for 1 h. After the incubation step, the Ab solution was removed; the surface was washed with PBS pH 7.2 and air-dried.

*S. aureus* was growth in TSB medium at 37° C. overnight. The bacterial suspension was centrifuged, the supernatant was discarded and the bacterium resuspended in 0.9% NaCl.

Measurement Procedure

First, the frequency for the dry biosensor was determined, and then the biosensor was immersed in 3 ml bacterial suspension for 58 minutes at room temperature. The sensor was removed from the suspension and air-dried and the new frequency was measured.

Results

Figure 22:
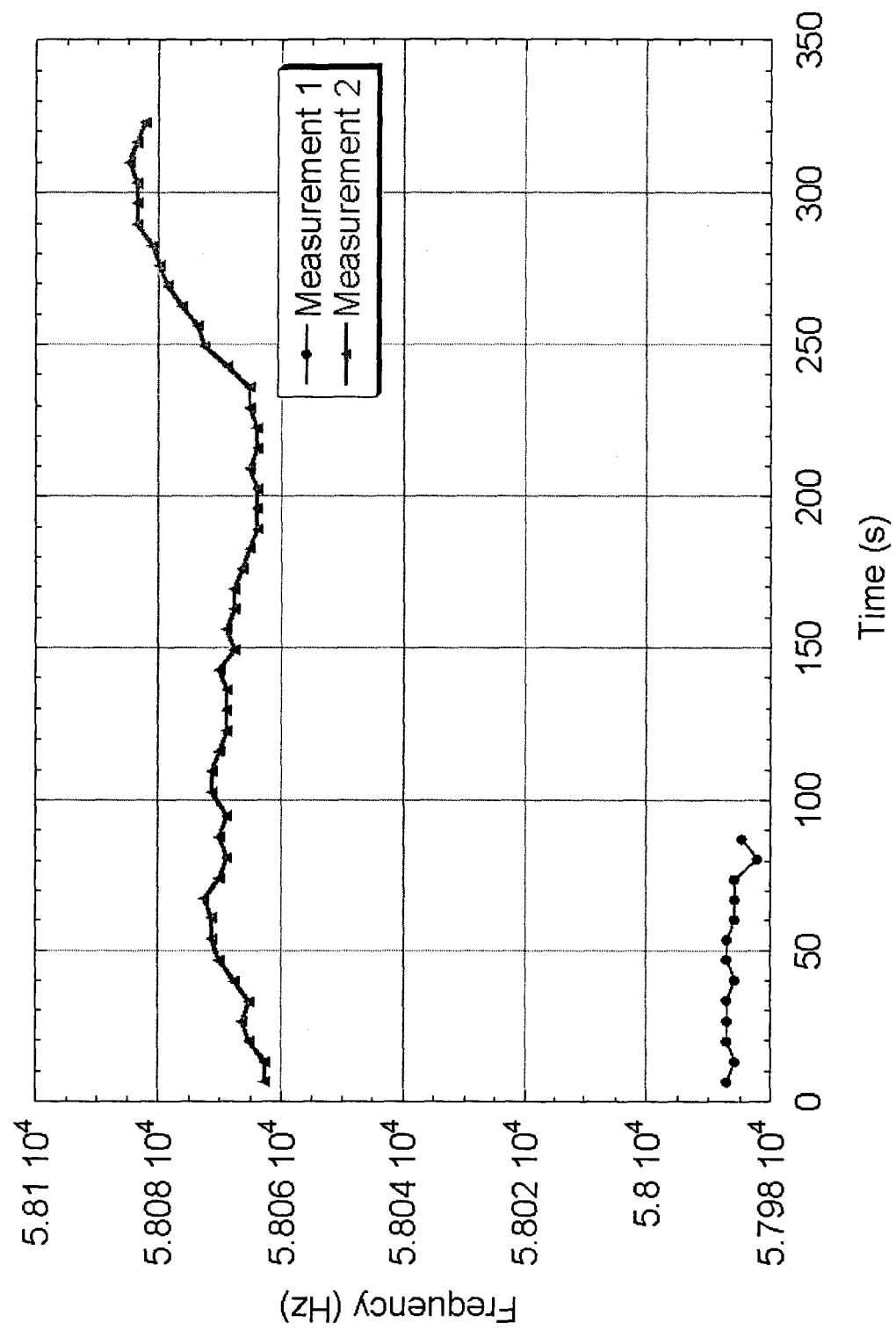
FIG. 22 shows a frequency shift from 57899 Hz to 58060 Hz when using METGLAS coated with a hydrophobic polymer.

As seen in FIG. 22, measurement 1 gave f 57899 Hz and measurement 2 gave f 58060 Hz.

The Δf is −60 Hz.

Conclusions

The results show a reverse response after immersion of biosensor in the target solution. At excitation of the sensor, a more flexible binding may cause orientation of the complex away from the surface of the sensor. This phenomenon may give rise to different oscillation direction, i.e., the oscillation of Ab-Ag complex is not in phase with the oscillation of sensor and this may explain the reverse response of the sensor.

A reverse response may also be obtained if the surface of the sensor becomes more rigid due to the binding of the target molecules Example 11

Biosensor for Detection of Lymphocytes Using METGLAS Coated with a Cationic Polymer Objective The objective of this example is to detect lymphocytes present in a target solution using a biosensor based on METGLAS coated with a cationic polymer and primary antibodies.

Materials and Methods

Polyethyleneimine, PEI, a high molecular weight water free polymer and glutaraldehyde sol 50% in water were purchased from Sigma-Aldrich. Mouse anti-ovine B and activated T cells was purchased from Serotec. Sheep blood was purchased from Statens Veterinärmedicinska Anstalt. Ficoll 400, Sodium diatrizoate and Balanced Salt Solution (BSS) were purchased from Sigma-Aldrich.

The METGLAS film was coated with PEI by dip coating in a 0.5% (w/w) PEI/methanol solution. The METGLAS was removed from the coating solution and air-dried to allow solvent evaporation. Chemical cross-linking was carried out by dip coating in a 2.5% (v/v) Glutaraldehyde/phosphate buffer saline solution, PBS, (pH 7.0) for 30 min at room temperature. The METGLAS was removed from the glutaraldehyde environment and placed in a heating oven at 100° C. for 4 minutes.

Finally, the monoclonal antibody (mAb) was immobilized onto the coated surface of the sensor. 200 μl stock solution of mAb (as received from Serotec) was added on the polymer layer and incubated at room temperature for 1 h. After the incubation step, the mAb solution was removed; the surface was washed with PBS pH 7.2 and air-dried.

Isolation of lymphocytes from whole sheep blood was carried out by density gradient separation technique. The separation medium containing ficoll and sodium diatrizoate has a density of 1.077 g/ml at room temperature. BSS (25 ml) was added to a centrifuge tube (50 ml) containing whole sheep blood (25 ml). After mixing by inverting of the tube, 25 ml of the blood sample was carefully layered onto 15 ml separation medium and centrifugation was performed at room temperature. The lymphocyte layer was carefully collected, washed with sterile PBS (2×) and resuspended in PBS (2.5 ml).

Measurement Procedure

First, the frequency for the dry biosensor was determined, and then the biosensor was immersed in 2.5 ml lymphocyte suspension for 30 minutes at room temperature. The sensor was removed from the suspension, air-dried and the new frequency was measured.

Results

Figure 23:
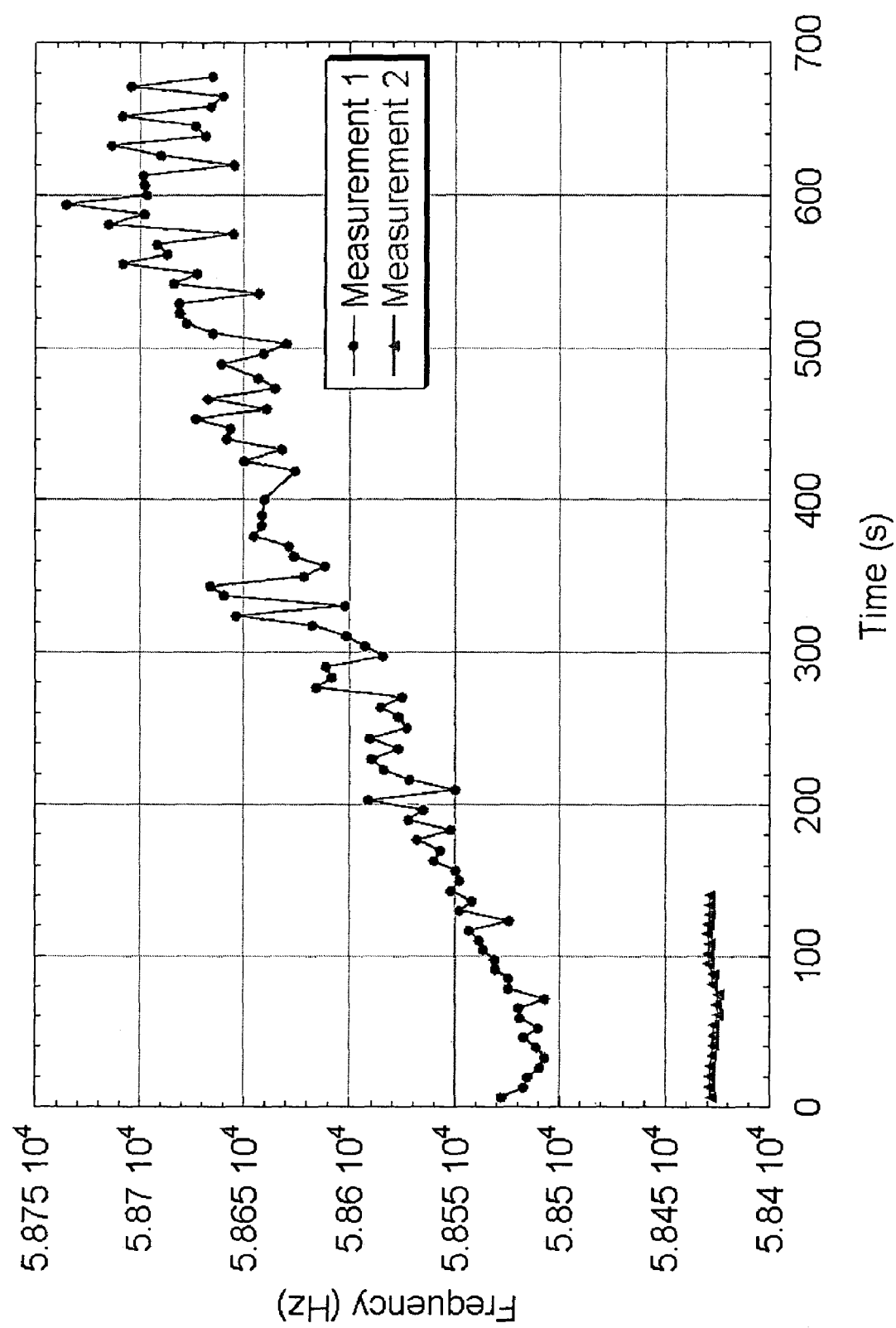
FIG. 23 shows a frequency shift from 58665 Hz to 58428 Hz when using METGLAS coated with a cationic polymer.

As seen in FIG. 23, measurement 1 gave f 58665 Hz and measurement 2 gave f 58428 Hz.

The Δf is 237 Hz.

Conclusions

The frequency shift indicates binding of the target species to the biosensor. The change in frequency shows the response of the sensor to additional surface mass load.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. An absorbent structure, comprising:
   at least one absorbent layer and
   at least one sensing device comprising a magnetoelastic film.

2. The absorbent structure of claim 1, wherein the least one absorbent layer comprises 0–100% of superabsorbent material.

3. The absorbent structure of claim 1, wherein the at least one absorbent layer comprises at least one acquisition layer and at least one storage layer.

4. The absorbent structure of claim 1, wherein the at least one absorbent layer comprises at least one drying layer, and wherein the absorbent layer optionally comprises a plurality of individual sheets and bonding means for joining said individual sheets.

5. The absorbent structure of claim 1, wherein the magnetoelastic film oscillates with a magnetoacoustic resonant frequency after the magnetoelastic film is excited in a magnetic field and the magnetic field is switched off.

6. The absorbent structure of claim 1, wherein the at least one sensing device is 1–20 sensing device(s).

7. The absorbent structure of claim 1, wherein the magnetoelastic film is a thin film, and wherein the magnetoelastic film comprises magnetostrictive material.

8. The absorbent structure of claim 7, wherein the magnetostrictive material is a magnetoelastic material, a soft magnetoelastic material, an amorphous magnetoelastic material, or a mixture thereof.

9. The absorbent structure of claim 1, wherein the magnetoelastic film is coated with a wetness sensitive polymer selected from the group consisting of linear and hydrophilic polymers or chemically/physically cross-linked swellable polymer gels based on polyvinyl alcohol, polyvinyl pyrrolidone, polyethylene oxide and co-polymers thereof; polyurethane; polyamides; starch and derivatives thereof; cellulose and derivatives thereof; polysaccharides; proteins; polyacrylonitrile; acrylate-based polymers; and mixtures thereof.

10. The absorbent structure of claim 1, wherein the magnetoelastic film is coated directly or indirectly with at least one detector molecule adapted to detect at least one target biological and/or chemical analyte.

11. An absorbent article comprising
the absorbent structure of claim 1,
a fluid-permeable top sheet, and
an essentially fluid-impermeable bottom sheet.

12. A diaper or pants-type diaper, comprising
the absorbent structure of claim 1,
a front-part,
a back-part, and
a crotch-part between the front and back-parts.

13. The diaper pants-type diaper of claim 12, wherein the absorbent structure comprises 1–10 sensing device(s).

14. An absorbent article comprising the absorbent structure of claim 1.

15. The absorbent article of claim 14, wherein the absorbent structure comprises
5–100% cellulose fibers, wherein said cellulose fibers are mainly comprised of fibers of chemothermomechanically-produced pulp, and between 0–95% superabsorbent material,
calculated on the total weight of the structure in a dry state.

16. A sensoring absorbent system, comprising
the absorbent structure of claim 1, and
a hand held unit comprising an excitation coil generating a magnetic field to magnetize said magnetoelastic film and optionally a pick-up coil to detect the magnetoacoustic resonant frequency.

17. The sensoring absorbent system according to claim 16, wherein the hand held unit comprises the excitation coil and the pick-up coil.

18. A method for detecting wetness, moisture, or humidity, and/or at least one biological and/or chemical analyte in an absorbent structure of claim 1, comprising the steps of
a) providing an absorbent structure of claim 1,
b) applying a magnetic field,
c) exciting the magnetoelastic film in the at least one sensing device in the absorbent structure,
d) switching the magnetic field off,
e) recording magnetoacoustic resonant frequency,
f) optionally repeating step b) to e), and
g) detecting changes in the magnetoacoustic resonant frequency, so as to detect wetness, moisture, or humidity, and/or at least one biological and/or chemical analyte in the absorbent structure.

19. The method of claim 18, wherein the magnetic field is a pulsed magnetic field.

20. The method of claim 18, wherein the magnetoelastic film excited in step c) is excited by an excitation coil.

21. The method of claim 20, wherein the excitation coil is in a hand held unit, and wherein the hand held unit is 0–5 m from the absorbing structure when exciting the magnetoelastic film in step c).

22. The method of claim 18, wherein the recording in step e) is detected by a pick-up coil.

23. The method of claim 22, wherein the pick-up coil is in a hand held unit, and wherein the hand held unit is 0–5 m from the absorbent structure when recording the magnetoacoustic resonant frequency in step e).

24. A wetness sensing device for detecting wetness, wherein said wetness sensing device comprises a magnetoelastic film, and said film being coated with a material that interacts with said wetness, resulting in a change in magnetoacoustic oscillations such that a first magnetoacoustic resonant frequency at said sensing device evoked when said sensing device is not influenced by wetness is different from a second magnetoacoustic frequency evoked when said sensing device is influenced with wetness.

25. The sensing device of claim 24, where said sensing device comprises protective packaging preventing the magnetoelastic film from being exposed to mechanical forces affecting the absorbent structure and which forces otherwise may affect the magentoacoustic resonant frequency of the magnetoelastic film.

26. The sensing device of claim 25, where said protective packaging is provided with one or more passages such that at least one chemical analyte found in body waste or body exudates can penetrate the package and reach the coating of the magentoelastic film.

27. The sensing device of claim 26, where said one or more passages are pores, slots, or holes.

28. The sensing device of claim 24, where said material is a mass changing material.

29. The sensing device of claim 28, where said material is a mass changing material.

30. The sensing device of claim 29, where said mass changing material changes its mass by dissolving when exposed to wetness.

31. The sensing device of claim 24, where said material is a polymer.

32. The sensing device of claim 31, where said polymer is a wetness sensitive polymer selected from the group consisting of linear and hydrophilic polymers or chemically/physically cross-linked swellable polymer gels based on polyvinyl alcohol, polyvinyl pyrrolindone, polyethylene oxide and copolymers thereof, polyurethane, polyamides, starch and derivatives thereof, cellulose and derivative thereof, polysaccharides, proteins, polyacrylonitrile, acrylate based polymers, and mixtures thereto.

33. The sensing device of claim 32, where said magnet is arranged in connection with the magnetoelastic film.

34. The sensing device of claim 24, where a permanent magnet is included in said sensing device.

35. The sensing device of claim 34, where said magnet is used for providing a magnetic bias field.

* * * * *

UNITED STATES PATENT AND TRADEMARK OFFICE
CERTIFICATE OF CORRECTION

| | | |
|---|---|---|
| PATENT NO. | : 7,176,344 B2 | Page 1 of 1 |
| APPLICATION NO. | : 10/655344 | |
| DATED | : February 13, 2007 | |
| INVENTOR(S) | : Ingrid Gustafson et al. | |

It is certified that error appears in the above-identified patent and that said Letters Patent is hereby corrected as shown below:

On the title page, Under (60) - Related U.S. Application Data, please delete "Jun. 9, 2002" and insert --September 6, 2002--.

Signed and Sealed this

Fifteenth Day of May, 2007

JON W. DUDAS
*Director of the United States Patent and Trademark Office*